United States Patent
Hamm et al.

(10) Patent No.: US 9,963,466 B2
(45) Date of Patent: *May 8, 2018

(54) SUBSTITUTED 5-MEMBERED HETEROCYCLIC ANALOGS AS PROTEASE ACTIVATED RECEPTOR 4 (PAR-4) ANTAGONISTS

(71) Applicant: Vanderbilt University, Nashville, TN (US)

(72) Inventors: Heidi E. Hamm, Nashville, TN (US); Shaun R. Stauffer, Nashville, TN (US); Craig W. Lindsley, Brentwood, TN (US); Matthew T. Duvernay, Nashville, TN (US); Kayla J. Temple, Spring Hill, TN (US)

(73) Assignee: Vanderbilt University, Nashville, TN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/452,686

(22) Filed: Mar. 7, 2017

(65) Prior Publication Data

US 2017/0253617 A1 Sep. 7, 2017

Related U.S. Application Data

(60) Provisional application No. 62/304,827, filed on Mar. 7, 2016.

(51) Int. Cl.
*C07D 513/04* (2006.01)

(52) U.S. Cl.
CPC .................................. *C07D 513/04* (2013.01)

(58) Field of Classification Search
CPC .................................................. C07D 513/04
See application file for complete search history.

(56) References Cited

U.S. PATENT DOCUMENTS 9,572,794 B2 * 2/2017 Hamm ................ A61K 31/5025

FOREIGN PATENT DOCUMENTS

| EP | 0667345 B1 | 9/1999 |
| EP | 1166785 A1 | 1/2002 |
| WO | WO 2013/163248 A1 | 10/2013 |
| WO | WO 2013/163279 A1 | 10/2013 |
| WO | WO 2014/173859 A3 | 10/2014 |
| WO | WO 2015/124570 A1 | 8/2015 |

OTHER PUBLICATIONS

Bonaca MP et al, Vorapaxar in Patients with Peripheral Artery Disease:Results from TRA2°P-TIMI 50; Circulation, 127 (14): 1522-9 (2013).
Braga, A. D., Miranda, J. P., Ferreira, G. M., Bilheiro, R. P., Duarte, I. D., Francischi, J. N., and Klein, A. (2010) Blockade of proteinase-activated receptor-4 inhibits the eosinophil recruitment induced by eotaxin-1 in the pleural cavity of mice, Pharmacology 86, 224-230.
Busso, N., Morard, C., Salvi, R., Peclat, V., and So, A. (2003) Role of the tissue factor pathway in synovial inflammation, Arthritis and rheumatism 48, 651-659.
Chen, H.S. et al, "Synthesis and platelet activity", J. Bioorg. Med. Chem., 16: 1262-1278 (2008).
Covic, L., et al. (2000) Biphasic kinetics of activation and signaling for PAR1 and PAR4 thrombin receptors in platelets, Biochemistry 39, 5458-5467.
Dabek, M., Ferrier, L., Roka, R., Gecse, K., Annahazi, A., Moreau, J., Escourrou, J., Cartier, C., Chaumaz, G., Leveque, M., Ait-Belgnaoui, A., Wittmann, T., Theodorou, V., and Buena, L. (2009) Luminal cathepsin G and protease-activated receptor 4: a duet involved in alterations of the colonic epithelial barrier in ulcerative colitis, The American journal of pathology 175, 207-214.
Duvemay, M., et al. (2013). Protease-activated receptor (PAR) 1 and PAR4 differentially regulate factor V expression from human platelets, Molecular Pharmacology 83, 781-792.
Falker, K., et al. (2011) Protease-activated receptor 1 (PAR1) signalling desensitization is counteracted via PAR4 signalling in human platelets, The Biochemical Journal 436, 469-480.
Frenette, P. S., Mayadas, T. N., Rayburn, H., Hynes, R. O., and Wagner, D. D. (1996) Susceptibility to infection and altered hematopoiesis in mice deficient in both P- and E-selectins, Cell 84, 563-574.
Gecse, K., Roka, R., Ferrier, L., Leveque, M., Eutamene, H., Cartier, C., Ait-Belgnaoui, A., Rosztoczy, A., Izbeki, F., Fioramonti, J., Wittmann, T., and Bueno, L. (2008) Increased faecal serine protease activity in diarrhoeic IBS patients: a colonic lumenal factor impairing colonic permeability and sensitivity, Gut 57, 591-599.
Gomides, L. F., Duarte, I. D., Ferreira, R. G., Perez, A. C., Francischi, J. N., and Klein, A. (2012) Proteinase-activated receptor-4 plays a major role in the recruitment of neutrophils induced by trypsin or carrageenan during pleurisy in mice, Pharmacology 89, 275-282.
Gomides, L. F., Lima, O. C., Matos, N. A., Freitas, K. M., Francischi, J. N., Tavares, J. C., and Klein, A. (2014) Blockade of proteinase-activated receptor 4 inhibits neutrophil recruitment in experimental inflammation in mice, Inflammation research : official journal of the European Histamine Research Society . . . [et al.] 63, 935-941.
Hattori, R., Hamilton, K. K., Fugate, R. D., McEver, R. P., and Sims, P. J. (1989) Stimulated secretion of endothelial von Willebrand factor is accompanied by rapid redistribution to the cell surface of the intracellular granule membrane protein GMP-140, The Journal of biological chemistry 264, 7768-7771.
Henrich-Noack, P., Riek-Burchardt, M., Baldauf, K., Reiser, G., and Reymann, K. G. (2006) Focal ischemia induces expression of protease-activated receptor1 (PAR1) and PAR3 on microglia and enhances PAR4 labeling in the penumbra, Brain research 1070, 232-241.
Houle, S., Papez, M. D., Ferazzini, M., Hollenberg, M. D., and Vergnolle, N. (2005) Neutrophils and the kallikrein-kinin system in proteinase-activated receptor 4-mediated inflammation in rodents, British journal of pharmacology 146, 670-678.

(Continued)

*Primary Examiner* — Laura L. Stockton
(74) *Attorney, Agent, or Firm* — Stites & Harbison PLLC; Richard S. Myers, Jr.

(57) ABSTRACT

Embodiments of the invention include compounds and compositions thereof to inhibit protease activated receptor-4. Also described are methods of preparation of compositions and methods for treating diseases related to thrombotic disorders by administration of the composition.

25 Claims, No Drawings

(56) References Cited

OTHER PUBLICATIONS

Kahn, M. L., et al. (1998) A dual thrombin receptor system for platelet activation, Nature 394, 690-694.

Kolpakov, M. A., Rafiq, K., Guo, X., Hooshdaran, B., Wang, T., Vlasenko, L., Bashkirova, Y. V., Zhang, X., Chen, X., Iftikhar, S., Libonati, J. R., Kunapuli, S. P., and Sabri, A. (2016) Protease-activated receptor 4 deficiency offers cardioprotection after acute ischemia reperfusion injury, Journal of molecular and cellular cardiology 90, 21-29.

Lee, F-Y. et al., "Synthesis of I-Benzyl-3-(5'-hydroxymethyl-2'-furyl)indazole Analogues as Novel Antiplatelet Agents", J. Med. Chem., 44(22):3746-3749 (2001).

Mao, Y., Zhang, M., Tuma, R. F., and Kunapuli, S. P. (2010) Deficiency of PAR4 attenuates cerebral ischemic/reperfusion injury in mice, Journal of cerebral blood flow and metabolism : official journal of the International Society of Cerebral Blood Flow and Metabolism 30, 1044-1052.

McDougall, J. J., Zhang, C., Cellars, L., Joubert, E., Dixon, C. M., and Vergnolle, N. (2009) Triggering of proteinase-activated receptor 4 leads to joint pain and inflammation in mice, Arthritis and rheumatism 60, 728-737.

Morrow DA et al, Efficacy and Safety of Vorapaxar in Patients With Prior Ischemic Stroke; Stroke 44(3):691-8 (2013).

Nakanishi-Matsui, M., et al. (2000) PAR3 is a cofactor for PAR4 activation by thrombin, Nature 404, 609-613.

Rohatgi, T., Sedehizade, F., Sabel, B. A., and Reiser, G. (2003) Protease-activated receptor subtype expression in developing eye and adult retina of the rat after optic nerve crush, Journal of neuroscience research 73, 246-254.

Sambrano, G. R., et al. (2001) Role of thrombin signalling in platelets in haemostasis and thrombosis, Nature 413, 74-78.

Scirica BM et al, Vorapaxar for secondary prevention of thrombotic events for patients with previous myocardial infarction: a prespecified subgroup analysis of the TRA 2°P-TIMI 50 trial; Lancet., 380(9850): 1317-24 (2012).

Slofstra, S. H., Bijlsma, M. F., Groot, A. P., Reitsma, P. H., Lindhout, T., ten Cate, H., and Spek, C. A. (2007) Protease-activated receptor-4 inhibition protects from multiorgan failure in a murine model of systemic inflammation, Blood 110, 3176-3182.

So, A. K., Varisco, P. A., Kemkes-Mallhes, B., Herkenne-Morard, C., Chobaz-Peclat, V., Gerster, J. C., and Busso, N. (2003) Arthritis is linked to local and systemic activation of coagulation and fibrinolysis pathways, J Thromb Haemost 1, 2510-2515.

Soslau, G., Class, R., Morgan, D. A., Foster, C., Lord, S. T., Marchese, P., and Ruggeri, Z. M. (2001) Unique pathway of thrombin-induced platelet aggregation mediated by glycoprotein Ib, The Journal of biological chemistry 276, 21173-21183.

Soslau, G., Goldenberg, S. J., Class, R., and Jameson, B. (2004) Differential activation and inhibition of human platelet thrombin receptors by structurally distinct alpha-, beta- and gamma-thrombin, Platelets 15, 155-166.

Strande, J. L., Hsu, A., Su, J., Fu, X., Gross, G. J., and Baker, J. E. (2008) Inhibiting protease-activated receptor 4 limits myocardial ischemia/reperfusion injury in rat hearts by unmasking adenosine signaling, The Journal of pharmacology and experimental therapeutics 324, 1045-1054.

Subramaniam, M., Frenette, P. S., Saffaripour, S., Johnson, R. C., Hynes, R. O., and Wagner, D. D. (1996) Defects in hemostasis in P-selectin-deficient mice, Blood 87, 1238-1242.

Tricoci, P. et al, Thrombin-Receptor Antagonist Vorapaxar in Acute Coronary Syndromes; N. Eng. J. Med., 366(1):20-33 (2012).

Vergnolle, N., Derian, C. K., D'Andrea, M. R., Steinhoff, M., and Andrade-Gordon, P. (2002) Characterization of thrombin-induced leukocyte rolling and adherence: a potential proinflammatory role for proteinase-activated receptor-4, Journal of immunology 169, 1467-1473.

Vretenbrant, K., et al. (2007). Platelet activation via PAR4 is involved in the initiation of thrombin generation and in clot elasticity development, Thrombosis and haemostasis 97, 417-424.

Weber, C. R., and Turner, J. R. (2007) Inflammatory bowel disease: is it really just another break in the wall?, Gut 56, 6-8; Podolsky, D. K. (2002) Inflammatory bowel disease, The New England journal of medicine 347, 417-429.

38. Whellan DJ et al, Vorapaxar in Acute Coronary Syndrome Patients Undergoing Coronary Artery Bypass Graft Surgery; J Am Coll Cardiol., 63(11): 1048-57(2014).

Wu, C-C. et al, "Selective Inhibition of Protease-activated Receptor 4-dependent Platelet Activation by YD-3", Thromb. Haemost., 87: 1026-1033 (2002).

\* cited by examiner

SUBSTITUTED 5-MEMBERED HETEROCYCLIC ANALOGS AS PROTEASE ACTIVATED RECEPTOR 4 (PAR-4) ANTAGONISTS

PRIOR APPLICATIONS

This application claims benefit to U.S. Patent Application No. 62/304,827, filed Mar. 7, 2017, the contents of which are incorporated herein by reference in their entirety.

GOVERNMENT SUPPORT

This invention was made with support from grants from the National Institutes of Health grant numbers NS081669 and NS082198. The United States Government has certain rights to this invention.

FIELD OF THE INVENTION

Embodiments of the present invention relate to novel compounds as selective protease activated receptor 4 (PAR4) antagonists. The compounds of the present invention are useful in preventing or treating thromboembolic disorders. Other embodiments of the present invention relate to pharmaceutical compositions containing the compounds of the present invention as well as methods of using the same.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharide factor Xa inhibitors, direct thrombin inhibitors such as Bivalrudin, and antiplatelet agents such as integrin αIIbβ3 inhibitors, aspirin, clopidogrel (PLAVIX®), and Vorapaxar (Zontivity®). Additionally, current anti-platelet therapies have limitations including increased risk of bleeding as well as partial efficacy (relative cardiovascular risk reduction in the 20 to 30% range). Thus, there is an unmet medical need for safe and efficacious oral or parenteral antithrombotics for the prevention and treatment of a wide range of thromboembolic disorders.

Thrombin is a protease at the center of coagulation. Activation of platelets by thrombin, the terminal product of the coagulation cascade, is an essential component of the hemostatic response. In addition to the activation of coagulation factors and fibrinogen, thrombin regulates cellular activities through stimulation of the G-protein coupled protease activated receptors (PARs). These receptors are activated by cleavage by thrombin, and in a unique mechanism, the new amino terminus is the activating "tethered ligand". This causes irreversible activation of the receptors. In humans, platelets express two PARs, PAR1 and PAR4. PAR1 is ubiquitously expressed, and PAR1 signaling underlies not only coagulation, but also inflammation, pain, healing and cancer metastasis, while the expression of PAR4 is much more restricted, mainly to platelets and expression in certain brain areas and vascular beds after stress.

PAR1 is the "high affinity" thrombin receptor, while PAR4 requires much higher thrombin for activation, levels probably only seen in a platelet clot. Due to this difference in affinity, PAR1 and PAR4 are engaged in a progressive manner, with PAR1 activated at low thrombin concentrations and PAR4 recruited at higher thrombin concentrations. Because of the delay in activation we hypothesize that PAR4 antagonism might not affect hemostasis as potently and thus may be a better therapeutic target than PAR1.

Inhibitors of PAR1 have been investigated extensively, and several compounds, including Vorapaxar and atopaxar have advanced into late stage clinical trials. Recently, in the TRACER phase III trial among non-ST-segment elevation acute coronary syndromes (ACS) patients, Vorapaxar did not significantly reduce the primary composite endpoint, and in fact was halted early due to a significant increase in the risk of major bleeding, including intracranial hemorrhage (Tricoci, P. et al, *N. Eng. J. Med.*, 366(1):20-33 (2012). However, among non-ST-segment ACS patients undergoing CABG specifically, Vorapaxar was associated with a significant reduction in ischemic events and no significant increase in major CABG-related bleeding (Whellan D J et al, *J Am Coll Cardiol.*, 63(11): 1048-57(2014). The TRA 2P-TIMI 50 trial demonstrated that in patients with myocardial infarction, Vorapaxar reduced the risk of cardiovascular death or ischaemic events with a significant increase in moderate to severe bleeding when added to the standard anti-platelet therapy (Scirica B M et al, *Lancet.*, 380(9850): 1317-24 (2012). Similar results were collected among patients with peripheral artery disease demonstrating significant beneficial effects on limb ischemia and peripheral revascularization with increased risk of bleeding (Bonaca M P et al, *Circulation*, 127(14): 1522-9 (2013). However, among patients with prior ischemic stroke adding Vorapaxar to the standard of care increased the risk of intracranial hemorrhage without improvement in major vascular events (Morrow D A et al, *Stroke* 44(3):691-8 (2013). Therefore, even though the PAR-1 antagonist Vorapaxar (Zontivity™) was approved by the FDA as the first in class protease activated receptor antagonist, its potential application is severely limited by the bleeding side effects and increased risk of hemorrhagic stroke. The inability of PAR1-inhibited platelets to sense and respond to low levels of thrombin is likely a contributing factor to the bleeding events observed in patients using Vorapaxar (Zontivity™).

Mice express PAR3 and PAR4 on their platelet surface. PAR3 itself does not signal but serves as a cofactor, enhancing PAR4 activation by thrombin (Kahn, M. L., et al. (1998) A dual thrombin receptor system for platelet activation, *Nature* 394, 690-694; Nakanishi-Matsui, M., et al. (2000) PAR3 is a cofactor for PAR4 activation by thrombin, *Nature* 404, 609-613.) Intriguingly, PAR4−/− mice are protected from thrombosis and cerebral ischemia/reperfusion injury, have prolonged tail bleeding times, but no bleeding disorder. These phenotypes in mice are consistent with the fact PAR4 knockout results in a platelet that is incapable of responding to thrombin (Sambrano, G. R., et al. (2001) Role of thrombin signalling in platelets in haemostasis and thrombosis, Nature 413, 74-78.). These data combined with the fact that PAR4 is the lower affinity receptor and thus not engaged until later stages of hemostasis and possibly thrombosis, suggest that PAR4 is an attractive target for a safer anti-platelet therapy in thrombosis and cerebrovascular injury. Fortunately in humans both PAR1 and PAR4 are expressed on platelets, allowing for a dual thrombin receptor system. This presents a unique pharmacological opportunity, allowing inhibition of one PAR to preserve the platelet response to thrombin through the other, thereby perturbing but not eliminating thrombin-mediated platelet signaling. The physiologic role for PAR4 in hemostasis and thrombosis has not been fully established in humans; however, the pharmacodynamics of this receptor suggests that it may contribute to the pathophysiology of thrombosis. The signaling effectors engaged by PAR1 and PAR4 are essentially redundant; however responses display differences in both magnitude and kinetics. PAR1 signaling quickly desensitizes after activation while PAR4 signaling persists (Falker, K., et al. (2011) Protease-activated receptor 1 (PAR1) signalling desensitization is counteracted via PAR4 signalling in human platelets, *The Biochemical Journal* 436, 469-480.). This is reflected in the $Ca^{2+}$ response which is rapid and transient downstream of PAR1, but slow and sustained downstream of PAR4 (Covic, L., et al. (2000) Biphasic kinetics of activation and signaling for PAR1 and PAR4 thrombin receptors in platelets, *Biochemistry* 39, 5458-5467.). Similar profiles were obtained for Protein Kinase C (PKC) and Rhokinase mediated phosphorylation with stronger and more sustained activity downstream of PAR4 activation. Importantly, this leads to greater integrin activation and more secretion through PAR4, which is capable of overcoming the PAR1 response when fully engaged (Duvernay, M., et al. (2013). Protease-activated receptor (PAR) 1 and PAR4 differentially regulate factor V expression from human platelets, *Molecular Pharmacology* 83, 781-792; Vretenbrant, K., et al. (2007). Platelet activation via PAR4 is involved in the initiation of thrombin generation and in clot elasticity development, *Thrombosis and haemostasis* 97, 417-424.). Due to the higher affinity of PAR1 for thrombin there is a sequential nature to PAR engagement by thrombin on the human platelet, with PAR1 activation prior to PAR4 as thrombin concentrations rise in response to vascular injury. With the redundancy in signaling, full inhibition of PAR4 activity would at best result in a partial reduction in the magnitude and duration of the platelet response to thrombin due to intact PAR1 signaling. In addition, inhibitors with partial antagonism of the PAR4 receptor would be expected to partly preserve PAR-4 mediated platelet signaling activation, therefore providing a means to further modulate efficacy and potency via PAR4 inhibition. In summary, based on the latent engagement and activation of PAR4 at higher thrombin concentrations and the observations from the animal studies described, we hypothesize that PAR4 antagonism may be a safer and better therapeutic approach than PAR1 to treat thrombotic disorders and cerebrovascular injury and potentially primary and secondary prevention.

There are several early reports of preclinical studies of PAR4 inhibitors. Lee, F-Y. et al., "Synthesis of 1-Benzyl-3-(5'-hydroxymethyl-2'-furyl)indazole Analogues as Novel Antiplatelet Agents", *J. Med. Chem.*, 44(22):3746-3749 (2001) discloses in the abstract that the compound:

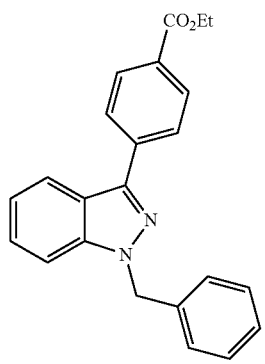

YD-3

"was found to be a selective and potent inhibitor or protease-activated receptor type 4 (PAR4)-dependent platelet activation."

YD-3 was also referenced in Wu, C-C. et al, "Selective Inhibition of Protease-activated Receptor 4-dependent Platelet Activation by YD-3", Thromb. Haemost., 87: 1026-1033 (2002). Also, see Chen, H. S. et al, "Synthesis and platelet activity", J. Bioorg. Med. Chem., 16: 1262-1278 (2008).

EP1166785 A1, EP0667345, WO 2013/163248 and WO 2013/163279, all incorporated herein by reference, disclose various compounds which are useful as inhibitors of platelet aggregation.

As indicated in WO 2014/173859 and WO 2015/124570, both of which are incorporated herein by reference, compounds of the present invention are useful for treating or preventing influenza virus type A infections. As indicated in WO 2015/124570, influenza is one of the most common infectious diseases in humans, occurring as seasonal epidemic and sporadic pandemic outbreaks. Annually, influenza A viruses (IAV) cause 3-5 million clinical infections and 200,000-500,000 fatal cases.

The hallmark of severe influenza virus infections is excessive inflammation of the lungs. Platelets are activated during influenza, but their role in influenza virus pathogenesis and inflammatory responses is unknown. Targeted gene deletion approaches and pharmacological interventions have been used to investigate the role of platelets during influenza virus infection in mice. Lungs of infected mice were massively infiltrated by aggregates of activated platelets. Platelet activation promoted IAV pathogenesis. Activating protease-activated receptor 4 (PAR-4), a platelet receptor for thrombin that is crucial for platelet activation, exacerbated influenza-induced acute lung injury and death. In contrast, deficiency in the major platelet receptor glycoprotein IIIa (GPIIIa) protected mice from death caused by influenza viruses, and treating the mice with a specific GPIIbIIIa antagonist, eptifibatide, had the same effect. Interestingly, mice treated with other anti-platelet compounds (such as antagonists of PAR-4, for example) were also protected from severe lung injury and lethal infections induced by several influenza strains. The intricate relationship between hemostasis and inflammation has major consequences in influenza virus pathogenesis, and anti-platelet drugs have been explored to develop new anti-inflammatory treatment against influenza virus infections.

Accordingly with the compounds of the present invention being antagonists of PAR-4, an object of the present invention relates to a method for the treatment of influenza A virus (IAV) infection in a subject in need thereof comprising administering the subject with a therapeutically effective amount of at least one anti-platelet agent of the present invention. As used herein, the term "influenza A virus infection" or "IAV infection" has its general meaning in the art and refers to the disease caused by an infection with an influenza A virus. In some embodiments of the invention, IAV infection is caused by influenza virus A that is H1N1, H2N2, H3N2 or H5N1. As used herein, an "anti-platelet agent" refers to members of a class of pharmaceuticals that inhibit platelet function, for example, by inhibiting the activation, aggregation, adhesion or granular secretion of platelets.

As indicated in WO 2013/163279, the PAR-4 antagonists of the present invention are useful as selective inhibitors of platelet aggregation, including stereoisomers, tautomers, pharmaceutically acceptable salts, solvates, or prodrug esters thereof.

Accordingly, in another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al., Medicine (Baltimore), 78(5):285-291 (1999); Levine M. et al, N. Engl. J. Med., 334(11):677-681 (1996); Blom, J. W. et al, JAMA, 293(6):715-722 (2005).) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer {i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular weight heparin preparations have been approved by the FDA for these indications.

Gamma-thrombin is a proteolytic product of alpha-thrombin cleavage by a serine protease. Cleavage results in the disruption of exosite I which interacts directly with the hirudin-like domain of its primary substrates fibrinogen and protease-activated receptor 1 (PAR1). As a result, gamma-thrombin selectively cleaves PAR4 in the nanomolar range, leaving PAR1 intact. See Soslau, G., Class, R., Morgan, D. A., Foster, C., Lord, S. T., Marchese, P., and Ruggeri, Z. M. (2001) Unique pathway of thrombin-induced platelet aggregation mediated by glycoprotein Ib, *The Journal of biological chemistry* 276, 21173-21183. Gamma-thrombin (Enzyme Research Laboratories, South Bend, Ind.) is produced by trypsin-sepharose cleavage of alpha-thrombin. To neutralize alpha-thrombin contamination, stock solutions of gamma-thrombin are preincubated with 1 unit/mL hirudin prior 100 fold dilution into the sample for platelet stimulation. This concentration of hirudin is capable of abolishing alpha-thrombin activity with no effect on the activity of gamma-thrombin. See Soslau, G., Goldenberg, S. J., Class, R., and Jameson, B. (2004) Differential activation and inhibition of human platelet thrombin receptors by structurally distinct alpha-, beta- and gamma-thrombin, *Platelets* 15, 155-166. Single point screens and concentration response curves are conducted with 316 nanomolar or 100 nanomolar gamma-thrombin using PAC1 and CD61p binding.

Embodiments of the present invention are also useful in reducing injury from myocardial ischemia/reperfusion. Decreased PAR1 mRNA and increased PAR4 mRNA detection in the rat brain after endothelin injection into the middle cerebral artery. SeeRohatgi, T., Sedehizade, F., Sabel, B. A., and Reiser, G. (2003) Protease-activated receptor subtype expression in developing eye and adult retina of the rat after optic nerve crush, *Journal of neuroscience research* 73, 246-254. Enhanced immunohistochemical labeling of PAR4 after endothelin injection into the middle cerebral artery in the border zone and the infarct zone. See Henrich-Noack, P., Riek-Burchardt, M., Baldauf, K., Reiser, G., and Reymann, K. G. (2006) Focal ischemia induces expression of protease-activated receptor1 (PAR1) and PAR3 on microglia and enhances PAR4 labeling in the penumbra, *Brain research* 1070, 232-241. Inhibition of PAR4 (P4pal 10 and trans-cinnamoyl-YPGKF) reduced infarct size in a rat model of myocardial ischemia/repurfusion injury. See Strande, J. L., Hsu, A., Su, J., Fu, X., Gross, G. J., and Baker, J. E. (2008) Inhibiting protease-activated receptor 4 limits myocardial ischemia/reperfusion injury in rat hearts by unmasking adenosine signaling, *The Journal of pharmacology and experimental therapeutics* 324, 1045-1054 PAR4 deficiency resulted in an 80% reduction in infarct volume following transient middle cerebral artery occlusion (MCAO). Mao, Y., Zhang, M., Tuma, R. F., and Kunapuli, S. P. (2010) Deficiency of PAR4 attenuates cerebral ischemia/reperfusion injury in mice, *Journal of cerebral blood flow and metabolism: official journal of the International Society of Cerebral Blood Flow and Metabolism* 30, 1044-1052. PAR4 deficiency resulted in reduced infarct size and more robust functional recovery in in vivo and ex vivo models of myocardial ischemia reperfusion injury. See Kolpakov, M. A., Rafiq, K., Guo, X., Hooshdaran, B., Wang, T., Vlasenko, L., Bashkirova, Y. V., Zhang, X., Chen, X., Iftikhar, S., Libonati, J. R., Kunapuli, S. P., and Sabri, A. (2016) Protease-activated receptor 4 deficiency offers cardioprotection after acute ischemia reperfusion injury, *Journal of molecular and cellular cardiology* 90, 21-29. PAR4 mediates proapoptotic signaling on isolated cardiomyocytes.

Embodiments of the present invention are also useful in the treatment of inflammation. For example, activation of PAR4 on epithelial cells leads to shape change, increased permeability, endothelial-dependent vasodilation and edema. PAR4 activation also induces Von Willebrand Factor and P-selectin expression in addition to cytokine production which is known to recruit platelets and leukocytes to sites of inflammation. See Subramaniam, M., Frenette, P. S., Saffaripour, S., Johnson, R. C., Hynes, R. O., and Wagner, D. D. (1996) Defects in hemostasis in P-selectin-deficient mice, *Blood* 87, 1238-1242; Frenette, P. S., Mayadas, T. N., Rayburn, H., Hynes, R. O., and Wagner, D. D. (1996) Susceptibility to infection and altered hematopoiesis in mice deficient in both P- and E-selectins, *Cell* 84, 563-574; and Hattori, R., Hamilton, K. K., Fugate, R. D., McEver, R. P., and Sims, P. J. (1989) Stimulated secretion of endothelial von Willebrand factor is accompanied by rapid redistribution to the cell surface of the intracellular granule membrane protein GMP-140, *The Journal of biological chemistry* 264, 7768-7771.

Leukocyte recruitment to endothelial cells at the site of inflammation is a hallmark of the inflammatory response. The first indicator for PAR4 role in inflammation comes from the imaging of leukocyte recruitment in an in vivo intravital microscopy system. Topical administration of thrombin to the mesenteric venule results in increased leukocyte rolling and adhesion. These results were recapitulated with PAR4-AP but not PAR1-AP. Moreover, intraperitoneal injection of PAR4-AP caused significant increase in extravascular leukocyte migration into the peritoneal cavity. See Vergnolle, N., Derian, C. K., D'Andrea, M. R., Steinhoff, M., and Andrade-Gordon, P. (2002) Characterization of thrombin-induced leukocyte rolling and adherence: a potential proinflammatory role for proteinase-activated receptor-4, *Journal of immunology* 169, 1467-1473. More recently, the PAR4 antagonist YPGKF-NH 2 (tcY-NH2) was shown to inhibit neutrophil migration into CXCL8, carrageenan (Cg), PAR4-AP, or Trypsin injected pleural cavities of mice. See Gomides, L. F., Lima, O. C., Matos, N. A., Freitas, K. M., Francischi, J. N., Tavares, J. C., and Klein, A. (2014) Blockade of proteinase-activated receptor 4 inhibits neutrophil recruitment in experimental inflammation in mice, *Inflammation research: official journal of the European Histamine Research Society . . .* [et al.] 63, 935-941; Gomides, L. F., Duarte, I. D., Ferreira, R. G., Perez, A. C., Francischi, J. N., and Klein, A. (2012) Proteinase-activated receptor-4 plays a major role in the recruitment of neutrophils induced by trypsin or carrageenan during pleurisy in mice, *Pharmacology* 89, 275-282. tcY-NH2 also blocks eosinophil recruitment after intrapleural injection of the chemokine Eotaxin-1. See Braga, A. D., Miranda, J. P., Ferreira, G. M., Bilheiro, R. P., Duarte, I. D., Francischi, J. N., and Klein, A. (2010) Blockade of proteinase-activated receptor-4 inhibits the eosinophil recruitment induced by eotaxin-1 in the pleural cavity of mice, *Pharmacology* 86, 224-230.

Additionally, inflammatory arthritis is a localized pathology characterized by increased thrombin generation and coagulation factor activation, even compared to osteoarthritis (mechanical as opposed to immune induced inflammation). See So, A. K., Varisco, P. A., Kemkes-Matthes, B., Herkenne-Morard, C., Chobaz-Peclat, V., Gerster, J. C., and Busso, N. (2003) Arthritis is linked to local and systemic activation of coagulation and fibrinolysis pathways, *J Thromb Haemost* 1, 2510-2515. Tissue factor levels and activity are increase in the synovial fluid of patients with rheumatoid arthritis. See Busso, N., Morard, C., Salvi, R., Peclat, V., and So, A. (2003) Role of the tissue factor pathway in synovial inflammation, *Arthritis and rheumatism* 48, 651-659. Recent work seeking to describe how excess thrombin contributes to disease progression has indicated PAR4 as a possible modulator. PAR4 knock out drastically reduces the inflammatory response in a mouse model of tissue factor induced inflammatory arthritis. See Busso, N., Chobaz-Peclat, V., Hamilton, J., Spee, P., Wagtmann, N., and So, A. (2008) Essential role of platelet activation via protease activated receptor 4 in tissue factor-initiated inflammation, *Arthritis research & therapy* 10, R42. Similar results are obtained in a kaolin/carrageenan induced model of inflammatory arthritis where PAR4 inhibition with a pepducin antagonist reduces indices of inflammatory arthritis. In the same study, direct injection of PAR4-AP induced joint swelling and hyperalgesia. See McDougall, J. J., Zhang, C., Cellars, L., Joubert, E., Dixon, C. M., and Vergnolle, N. (2009) Triggering of proteinase-activated receptor 4 leads to joint pain and inflammation in mice, *Arthritis and rheumatism* 60, 728-737. Similar results were obtained in general rat hindpaw carrageenan injected model of inflammation. Pepducin P4pal-10 and palmitoly-SGRRY-GHALR both reduced edema and granulocyte recruitment and direct injection of PAR4-AP caused edema and granulocyte recruitment. The indicated physiologic effect of PAR4 activation can be mediated through either platelets or neutrophils, both of which express PAR4. Yet, depletion of neutrophils significantly reduced PAR4-AP induced edema. See Houle, S., Papez, M. D., Ferazzini, M., Hollenberg, M. D., and Vergnolle, N. (2005) Neutrophils and the kallikrein-kinin system in proteinase-activated receptor 4-mediated inflammation in rodents, *British journal of pharmacology* 146, 670-678. These results indicate PAR4 activation on neutrophils as a pivotal event in inflammatory responses in the joint.

The compounds of the present invention are also useful in the treatment of sepsis. Sepsis is characterized by systemic inflammation and disseminated intravascular coagulation (DIC), the so-called Schwartzman reaction. In an endotoxin induced model of murine sepsis, P4pal-10 (PAR4 inhibitor) but not Plpal-12 (PAR1 inhibitor) reduced several indicators of organ failure and neutrophil influx, which are characteristic of the pathology. See Slofstra, S. H., Bijlsma, M. F., Groot, A. P., Reitsma, P. H., Lindhout, T., ten Cate, H., and Spek, C. A. (2007) Protease-activated receptor-4 inhibition protects from multiorgan failure in a murine model of systemic inflammation, *Blood* 110, 3176-3182. The Schwartzman reaction involves the interplay between immune and coagulation systems. PAR4 is expressed on neutrophils and platelets, which represent sentinels of each system respectively. In order to determine where PAR4 inhibition was exerting its effect on the system, mice were depleted of either neutrophils or platelets. In neutrophil depleted mice the protective effects of P4pal-10 were abolished indicating that PAR4 activation on neutrophils is pivotal to organ damage associated with DIC.

The compounds of the present invention are also useful in the treatment of inflammatory bowel disease. Inflammatory bowel diseases such as Chrone's and ulcerative colitis are characterized by increased permeability of the intestinal epithelial barrier, penetration of luminal products, and an immune response characterized by neutrophil invasion and cytokine driven inflammation. See Weber, C. R., and Turner, J. R. (2007) Inflammatory bowel disease: is it really just another break in the wall?, *Gut* 56, 6-8; Podolsky, D. K. (2002) Inflammatory bowel disease, *The New England journal of medicine* 347, 417-429. Fecal supernatants from patients with ulcerative colitis were shown to have abnormally high serine protease activity. See Gecse, K., Roka, R., Ferrier, L., Leveque, M., Eutamene, H., Cartier, C., Ait-Belgnaoui, A., Rosztoczy, A., Izbeki, F., Fioramonti, J., Wittmann, T., and Bueno, L. (2008) Increased faecal serine protease activity in diarrhoeic IBS patients: a colonic lumenal factor impairing colonic permeability and sensitivity, *Gut* 57, 591-599. Both PAR4 and its neutrophil derived specific agonist Cathepsin G are over-expressed in human colonic biopsies. Intracolonic infusion of fecal supernatants from ulcerative colitis patients induced para cellular permeability that was blocked with a PAR4 antagonist or a Cathepsin G inhibitor. See Dabek, M., Ferrier, L., Roka, R., Gecse, K., Annahazi, A., Moreau, J., Escourrou, J., Cartier, C., Chaumaz, G., Leveque, M., Ait-Belgnaoui, A., Wittmann, T., Theodorou, V., and Bueno, L. (2009) Luminal cathepsin G and protease-activated receptor 4: a duet involved in alterations of the colonic epithelial barrier in ulcerative colitis, *The American journal of pathology* 175, 207-214. In the same study the PAR4-AP was capable of inducing similar para cellular permeability.

SUMMARY OF THE INVENTION

The present inventors have discovered that the substituted 5-membered heterocyclic analogs of the present invention are PAR4 antagonists (both full and partial), which inhibit platelet aggregation.

Accordingly, the present invention provides novel compounds that are PAR4 antagonists and are useful as selective inhibitors of platelet aggregation, including stereoisomers, tautomers, pharmaceutically acceptable salts, solvates, or prodrug esters thereof.

In accordance with the purpose(s) of the invention, as embodied and described herein, the invention, in one aspect, relates to compounds useful as protease activated receptor-4 (PAR4) antagonists, methods of making same, pharmaceutical compositions comprising same, and methods of treating disorders associated with PAR4 activity. Further disclosed are methods and pharmaceutical compositions useful for treating a disease related to PAR4 activity.

Embodiments of the present invention relate to compounds and compositions that are PAR4 antagonists. Compounds and compositions of the present invention are also useful in preventing and treating thromboembolic disorders, including arterial thrombosis.

The present invention also relates to pharmaceutical compositions that include compounds of the present invention, and methods of using compounds and compositions of the present invention.

Included in the present invention are pharmaceutical compositions comprising a pharmaceutically acceptable carrier and at least one of the compounds of the present invention or stereoisomers, tautomers, pharmaceutically acceptable salts, solvates, or prodrug esters thereof.

Another embodiment of the present invention is a method for the treatment or prophylaxis of thrombosis, and/or thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrug esters thereof.

Another embodiment of the present invention are the compounds described herein or or stereoisomers, tautomers, pharmaceutically acceptable salts, solvates, or prodrug esters thereof, for use in therapy.

Another embodiment of the present invention is the use of the compounds of the present invention or stereoisomers, tautomers, pharmaceutically acceptable salts, solvates, or prodrug esters thereof, for the manufacture of a medicament for the treatment or prophylaxis of a thromboembolic disorder.

Other embodiments of the invention will be apparent from the following detailed description and claims.

DETAILED DESCRIPTION OF THE INVENTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

One embodiment of the present invention is compounds, stereoisomers, tautomers, salts, solvates, or prodrugs thereof, of formula (I), having the structure:

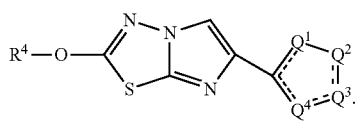

wherein:

$Q^1$ is selected from $CR^3$, N, N—Z, S, or O;

$Q^2$ is selected from $CR^3$, N, N—Z, S, or O;

$Q^3$ is selected from $CR^2$, N, N—Z, S, or O;

$Q^4$ is selected from $CR^1$, N, N—Z, S, or O;

$R^1$, $R^2$, and $R^3$ are independently selected from hydrogen, aryl, alkyl-aryl, substituted aryl, alkyl-substituted aryl, halo-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl, alkoxy, alkylalkoxy, methoxy, CN, halogen, $CONR^6R^7$, O—$CF_3$, $C(O_2)$-alkyl;

$R^1$ and $R^2$ may optionally jointly form a fused six-membered aryl or heteroaryl ring, optionally substituted with at least one $R^5$;

$R^4$ is methyl, $C_1$-$C_6$ alkyl;

$R^5$ is independently hydrogen, halogen, $C_1$-$C_6$ alkyl, cycloalkyl, alkoxy, methoxy, trifluoromethoxy, CN, amide, methyl, or trifluoromethyl;

$R^6$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

$R^7$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

Z is optionally present and is selected from hydrogen, aryl, substituted aryl, $C_1$-$C_4$ alkyl, $C_1$-$C_3$ polyhaloalky, CN, halogen, amide, $C_1$-$C_2$ alkyl-aryl, $C_1$-$C_2$ alkyl-substituted aryl, $C_1$-$C_2$ alkyl-CN, $C_1$-$C_2$ alkyl-halogen, $C_1$-$C_2$ alkyl-amide;

or a pharmaceutically acceptable salt, solvate, or polymorph thereof.

Also disclosed are pharmaceutical compositions that comprise a compound described herein or pharmaceutically acceptable salt, solvate, or polymorph thereof, and a pharmaceutically acceptable carrier. In one embodiment, the composition includes a compound having a structure represented by formula (I):

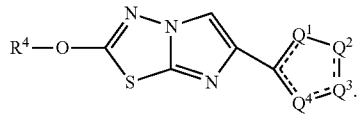

wherein:

$Q^1$ is selected from $CR^3$, N, N—Z, S, or O;

$Q^2$ is selected from $CR^3$, N, N—Z, S, or O;

$Q^3$ is selected from $CR^2$, N, N—Z, S, or O;

$Q^4$ is selected from $CR^1$, N, N—Z, S, or O;

$R^1$, $R^2$, and $R^3$ are independently selected from hydrogen, aryl, alkyl-aryl, substituted aryl, alkyl-substituted aryl, halo-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl, alkoxy, alkylalkoxy, methoxy, CN, halogen, $CONR^6R^7$, O—$CF_3$, $C(O_2)$-alkyl;

$R^1$ and $R^2$ may optionally jointly form a fused six-membered aryl or heteroaryl ring, optionally substituted with at least one $R^5$;

$R^4$ is methyl, $C_1$-$C_6$ alkyl;

$R^5$ is independently hydrogen, halogen, $C_1$-$C_6$ alkyl, cycloalkyl, alkoxy, methoxy, trifluoromethoxy, CN, amide, methyl, or trifluoromethyl;

$R^6$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

$R^7$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

Z is optionally present and is selected from hydrogen, aryl, substituted aryl, $C_1$-$C_4$ alkyl, $C_1$-$C_3$ polyhaloalky, CN, halogen, amide, $C_1$-$C_2$ alkyl-aryl, $C_1$-$C_2$ alkyl-substituted aryl, $C_1$-$C_2$ alkyl-CN, $C_1$-$C_2$ alkyl-halogen, $C_1$-$C_2$ alkyl-amide;

or a pharmaceutically acceptable salt, solvate, or polymorph thereof, and a pharmaceutically acceptable carrier.

Also disclosed are the pharmaceutical compositions described above, further comprising at least one additional drug or therapeutic agent. In certain embodiments of the preset invention, the at least one additional therapeutic agent(s) are an anti-platelet agent or a combination thereof. Examples of the anti-platelet agents include P2Y12 antagonists and/or aspirin. Preferably, the P2Y12 antagonists are clopidogrel, ticagrelor, or prasugrel. In another embodiment, the at least one additional therapeutic agent is an anticoagulant. Examples of the anticoagulant agent include FXa inhibitors or thrombin inhibitors. The FXa inhibitors may be, for example, apixaban or rivaroxaban. The thrombin inhibitor may be, for example, dabigatran.

Also disclosed herein are methods for the treatment of a disease state associated with PAR4 activity in a mammal comprising the step of administering to the mammal at least one compound in a dosage and amount effective to treat the disease state, the compound having a structure represented by formula (I):

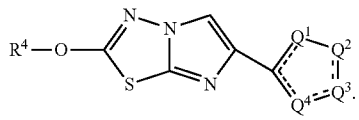

wherein:

$Q^1$ is selected from $CR^3$, N, N—Z, S, or O;
$Q^2$ is selected from $CR^3$, N, N—Z, S, or O;
$Q^3$ is selected from $CR^2$, N, N—Z, S, or O;
$Q^4$ is selected from $CR^1$, N, N—Z, S, or O;
$R^1$, $R^2$, and $R^3$ are independently selected from hydrogen, aryl, alkyl-aryl, substituted aryl, alkyl-substituted aryl, halo-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl, alkoxy, alkylalkoxy, methoxy, CN, halogen, $CONR^6R^7$, O—$CF_3$, $C(O_2)$-alkyl;

$R^1$ and $R^2$ may optionally jointly form a fused six-membered aryl or heteroaryl ring, optionally substituted with at least one $R^5$;

$R^4$ is methyl, $C_1$-$C_6$ alkyl;

$R^5$ is independently hydrogen, halogen, $C_1$-$C_6$ alkyl, cycloalkyl, alkoxy, methoxy, trifluoromethoxy, CN, amide, methyl, or trifluoromethyl;

$R^6$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

$R^7$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

Z is optionally present and is selected from hydrogen, aryl, substituted aryl, $C_1$-$C_4$ alkyl, $C_1$-$C_3$ polyhaloalky, CN, halogen, amide, $C_1$-$C_2$ alkyl-aryl, $C_1$-$C_2$ alkyl-substituted aryl, $C_1$-$C_2$ alkyl-CN, $C_1$-$C_2$ alkyl-halogen, $C_1$-$C_2$ alkyl-amide;

or a pharmaceutically acceptable salt, solvate, or polymorph thereof.

Also disclosed are methods for making a compound comprising the steps of providing a compound having a structure represented by formula (I):

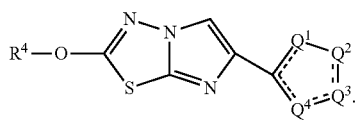

wherein:

$Q^1$ is selected from $CR^3$, N, N—Z, S, or O;
$Q^2$ is selected from $CR^3$, N, N—Z, S, or O;
$Q^3$ is selected from $CR^2$, N, N—Z, S, or O;
$Q^4$ is selected from $CR^1$, N, N—Z, S, or O;
$R^1$, $R^2$, and $R^3$ are independently selected from hydrogen, aryl, alkyl-aryl, substituted aryl, alkyl-substituted aryl, halo-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl, alkoxy, alkylalkoxy, methoxy, CN, halogen, $CONR^6R^7$, O—$CF_3$, $C(O_2)$-alkyl;

$R^1$ and $R^2$ may optionally jointly form a fused six-membered aryl or heteroaryl ring, optionally substituted with at least one $R^5$;

$R^4$ is methyl, $C_1$-$C_6$ alkyl;

$R^5$ is independently hydrogen, halogen, $C_1$-$C_6$ alkyl, cycloalkyl, alkoxy, methoxy, trifluoromethoxy, CN, amide, methyl, or trifluoromethyl;

$R^6$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

$R^7$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

Z is optionally present and is selected from hydrogen, aryl, substituted aryl, $C_1$-$C_4$ alkyl, $C_1$-$C_3$ polyhaloalky, CN, halogen, amide, $C_1$-$C_2$ alkyl-aryl, $C_1$-$C_2$ alkyl-substituted aryl, $C_1$-$C_2$ alkyl-CN, $C_1$-$C_2$ alkyl-halogen, $C_1$-$C_2$ alkyl-amide as shown in the Examples below, and wherein the variable are defined herein.

Also disclosed are the products of the disclosed methods of making.

Also disclosed are pharmaceutical compositions that comprise the products of the compounds disclosed herein.

Also disclosed are methods for the manufacture of a medicament for antagonizing PAR4 activity in a mammal comprising combining a compound having a structure represented by formula (I):

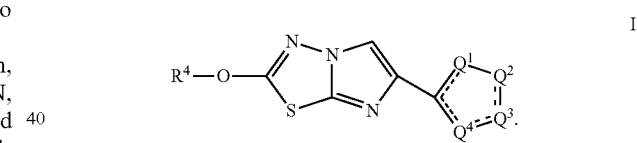

wherein:

$Q^1$ is selected from $CR^3$, N, N—Z, S, or O;
$Q^2$ is selected from $CR^3$, N, N—Z, S, or O;
$Q^3$ is selected from $CR^2$, N, N—Z, S, or O;
$Q^4$ is selected from $CR^1$, N, N—Z, S, or O;
$R^1$, $R^2$, and $R^3$ are independently selected from hydrogen, aryl, alkyl-aryl, substituted aryl, alkyl-substituted aryl, halo-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl, alkoxy, alkylalkoxy, methoxy, CN, halogen, $CONR^6R^7$, O—$CF_3$, $C(O_2)$-alkyl;

$R^1$ and $R^2$ may optionally jointly form a fused six-membered aryl or heteroaryl ring, optionally substituted with at least one $R^5$;

$R^4$ is methyl, $C_1$-$C_6$ alkyl;

$R^5$ is independently hydrogen, halogen, $C_1$-$C_6$ alkyl, cycloalkyl, alkoxy, methoxy, trifluoromethoxy, CN, amide, methyl, or trifluoromethyl;

$R^6$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

$R^7$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

Z is optionally present and is selected from hydrogen, aryl, substituted aryl, $C_1$-$C_4$ alkyl, $C_1$-$C_3$ polyhaloalky, CN, halogen, amide, $C_1$-$C_2$ alkyl-aryl, $C_1$-$C_2$ alkyl-substituted aryl, $C_1$-$C_2$ alkyl-CN, $C_1$-$C_2$ alkyl-halogen, $C_1$-$C_2$ alkyl-amide;

or a pharmaceutically acceptable salt, solvate, or polymorph thereof with a pharmaceutically acceptable carrier.

Also disclosed is a use for a compound of formula (I):

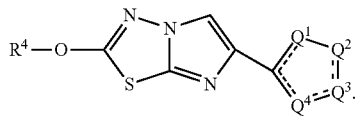

I wherein:
Q$^1$ is selected from CR$^3$, N, N—Z, S, or O;
Q$^2$ is selected from CR$^3$, N, N—Z, S, or O;
Q$^3$ is selected from CR$^2$, N, N—Z, S, or O;
Q$^4$ is selected from CR$^1$, N, N—Z, S, or O;
$R^1$, $R^2$, and $R^3$ are independently selected from hydrogen, aryl, alkyl-aryl, substituted aryl, alkyl-substituted aryl, halo-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl, alkoxy, alkylalkoxy, methoxy, CN, halogen, CONR$^6$R$^7$, O—CF$_3$, C(O$_2$)-alkyl;

$R^1$ and $R^2$ may optionally jointly form a fused six-membered aryl or heteroaryl ring, optionally substituted with at least one R$^5$;

$R^4$ is methyl, $C_1$-$C_6$ alkyl;

$R^5$ is independently hydrogen, halogen, $C_1$-$C_6$ alkyl, cycloalkyl, alkoxy, methoxy, trifluoromethoxy, CN, amide, methyl, or trifluoromethyl;

$R^6$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

$R^7$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

Z is optionally present and is selected from hydrogen, aryl, substituted aryl, $C_1$-$C_4$ alkyl, $C_1$-$C_3$ polyhaloalky, CN, halogen, amide, $C_1$-$C_2$ alkyl-aryl, $C_1$-$C_2$ alkyl-substituted aryl, $C_1$-$C_2$ alkyl-CN, $C_1$-$C_2$ alkyl-halogen, $C_1$-$C_2$ alkyl-amide;

or a pharmaceutically acceptable salt, solvate, or polymorph thereof; in the manufacture of a medicament for use in the treatment of a thromboembolic disorder or the primary or secondary prophylaxis of a thromboembolic disorder.

Also disclosed is the use of a compound of the following formula (I):

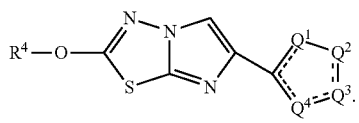

I wherein:
Q$^1$ is selected from CR$^3$, N, N—Z, S, or O;
Q$^2$ is selected from CR$^3$, N, N—Z, S, or O;
Q$^3$ is selected from CR$^2$, N, N—Z, S, or O;
Q$^4$ is selected from CR$^1$, N, N—Z, S, or O;
$R^1$, $R^2$, and $R^3$ are independently selected from hydrogen, aryl, alkyl-aryl, substituted aryl, alkyl-substituted aryl, halo-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl, alkoxy, alkylalkoxy, methoxy, CN, halogen, CONR$^6$R$^7$, O—CF$_3$, C(O$_2$)-alkyl;

$R^1$ and $R^2$ may optionally jointly form a fused six-membered aryl or heteroaryl ring, optionally substituted with at least one R$^5$;

$R^4$ is methyl, $C_1$-$C_6$ alkyl;

$R^5$ is independently hydrogen, halogen, $C_1$-$C_6$ alkyl, cycloalkyl, alkoxy, methoxy, trifluoromethoxy, CN, amide, methyl, or trifluoromethyl;

$R^6$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

$R^7$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

Z is optionally present and is selected from hydrogen, aryl, substituted aryl, $C_1$-$C_4$ alkyl, $C_1$-$C_3$ polyhaloalky, CN, halogen, amide, $C_1$-$C_2$ alkyl-aryl, $C_1$-$C_2$ alkyl-substituted aryl, $C_1$-$C_2$ alkyl-CN, $C_1$-$C_2$ alkyl-halogen, $C_1$-$C_2$ alkyl-amide;

or a pharmaceutically acceptable salt, solvate, or polymorph thereof in the treatment of a thromboembolic disorder or the primary or secondary prophylaxis of a thromboembolic disorder.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein, the term "subject" refers to a target of administration. The subject of the herein disclosed methods can be a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment of one or more thromboembolic disorder and/or any other disease state associated with PAR4 prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by a reduction of PAR4 activity" means having been subjected to a physical examination by a person of skill, for example, a physician, and found to have a condition that can be diagnosed or treated by a compound or composition that can antagonize PAR4 activity. Such a diagnosis can be in reference to a disorder, such as platelet aggregation, and the like, as discussed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "thrombotic disorders" refers to disorders characterized by formation of a thrombus that obstructs vascular blood flow. Examples of thrombotic disorders include stroke, myocardial infarction, stable or unstable angina, peripheral vascular disease, abrupt closure following angioplasty or stent placement and thrombosis induced by vascular surgery. Thrombotic disorders also include disorders characterized by formation of a thrombus caused by atrial fibrillation or inflammation.

The term "platelet aggregation" refers to the attachment of activated platelets one to another, which results in the formation of aggregates or clumps of activated platelets.

The term "thrombosis", as used herein, refers to formation or presence of a thrombus (pi. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

The term "stroke", as used herein, refers to embolic stroke or atherothrombotic stroke arising from occlusive thrombosis in the carotid communis, carotid interna, or intracerebral arteries.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents. Unless otherwise specified, the substituents are all independent from one another.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, thioether, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by a formula —C(O)H. Throughout this specification "C(O)" is a short hand notation for a carbonyl group, i.e., C=O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "heterocycle," as used herein refers to single and multi-cyclic aromatic or non-aromatic ring systems in which at least one of the ring members is other than carbon. Heterocycle includes pyridine, pyrimidine, pyrazine, furan, thiophene, pyrrole, isoxazole, isothiazole, pyrazole, oxazole, thiazole, imidazole, oxazole, oxadiazole including, for example, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, imidazothiadiazole, imidazooxadiazole, imidazothiazole, thiazolotriazole, and the like.

The term "hydroxyl" as used herein is represented by a formula —OH.

The term "thiol" as used herein is represented by a formula —SH.

The term "thioester" as used herein is represented by a formula —S—$CH_3$.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

In some aspects, a structure of a compound can be represented by a formula:

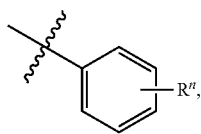

which is understood to be equivalent to a formula:

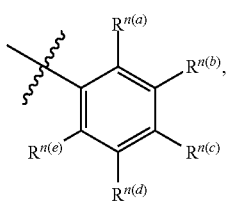

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance. Likewise, when a group R is defined as four substituents, R is understood to represent four independent substituents, $R^a$, $R^b$, $R^c$, and $R^d$. Unless indicated to the contrary, the substituents are not limited to any particular order or arrangement.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds, or pharmaceutically acceptable derivatives thereof, useful as antagonists of PAR4. In general, it is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

In one aspect, the invention relates to compounds having a structure represented by formula (I):

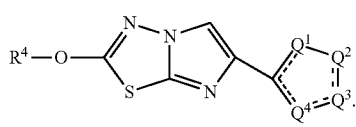

I wherein:
$Q^1$ is selected from $CR^3$, N, N—Z, S, or O;
$Q^2$ is selected from $CR^3$, N, N—Z, S, or O;
$Q^3$ is selected from $CR^2$, N, N—Z, S, or O;
$Q^4$ is selected from $CR^1$, N, N—Z, S, or O;
$R^1$, $R^2$, and $R^3$ are independently selected from hydrogen, aryl, alkyl-aryl, substituted aryl, alkyl-substituted aryl, halo-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl, alkoxy, alkylalkoxy, methoxy, CN, halogen, $CONR^6R^7$, O—$CF_3$, $C(O_2)$-alkyl;

$R^1$ and $R^2$ may optionally jointly form a fused six-membered aryl or heteroaryl ring, optionally substituted with at least one $R^5$;

$R^4$ is methyl, $C_1$-$C_6$ alkyl;

$R^5$ is independently hydrogen, halogen, $C_1$-$C_6$ alkyl, cycloalkyl, alkoxy, methoxy, trifluoromethoxy, CN, amide, methyl, or trifluoromethyl;

$R^6$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

$R^7$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;

Z is optionally present and is selected from hydrogen, aryl, substituted aryl, $C_1$-$C_4$ alkyl, $C_1$-$C_3$ polyhaloalky, CN, halogen, amide, $C_1$-$C_2$ alkyl-aryl, $C_1$-$C_2$ alkyl-substituted aryl, $C_1$-$C_2$ alkyl-CN, $C_1$-$C_2$ alkyl-halogen, $C_1$-$C_2$ alkyl-amide;

or a pharmaceutically acceptable salt, solvate, or polymorph thereof.

Also disclosed are compounds wherein $Q^1$ is $CR^3$, N, S, or O; and $Q^2$ is S, O, or N—Z.

Also disclosed are compounds wherein $Q^1$ is $CR^3$; $Q^2$ is N—Z; $Q^3$ is $CR^2$; $Q^4$ is $CR^1$; and $R^1$ and $R^2$ form a six-membered aryl.

Also disclosed are compounds wherein $Q^1$ is $CR^3$; $Q^2$ is $CR^3$; $Q^3$ is O; and $Q^4$ is N.

Also disclosed are compounds wherein $Q^1$ is $CR^3$; $Q^2$ is S; $Q^3$ is $CR^2$; $Q^4$ is $CR^1$; and $R^1$ and $R^2$ form a six-membered aryl.

Also disclosed are compounds wherein $Q^1$ is $CR^3$; $Q^2$ is O; $Q^3$ is N; and $Q^4$ is $CR^1$.

Also disclosed are compounds wherein $Q^1$ is $CR^3$; $Q^2$ is N; $Q^3$ is N; and $Q^4$ is $CR^1$.

Also disclosed are compounds wherein $Q^1$ is $CR^3$; $Q^2$ is N; $Q^3$ is $CR^2$; $Q^4$ is S.

Also disclosed are compounds wherein $Q^1$ is N; $Q^2$ is $CR^3$; $Q^3$ is $CR^2$; $Q^4$ is S.

Also disclosed are compounds wherein $Q^1$ is S; $Q^2$ is $CR^3$; $Q^3$ is $CR^2$; and $Q^4$ is $CR^1$.

Also disclosed are compounds wherein $Q^1$ is S, O, or N—Z; $Q^2$ is $CR^3$; $Q^3$ is $CR^2$; and $Q^4$ is $CR^1$.

Also disclosed are compounds wherein $Q^1$ is N; $Q^2$ is N—Z; $Q^3$ is $CR^2$; and $Q^4$ is $CR^1$.

Also disclosed are compounds wherein $Q^1$ is $CR^3$ or N; $Q^2$ is N—Z, O, or S; $Q^3$ is $CR^2$; $Q^4$ is $CR^1$; and $R^1$ and $R^2$ form a six-membered aryl.

Another embodiment of the present invention is a compound of claim 1, of the following formula:

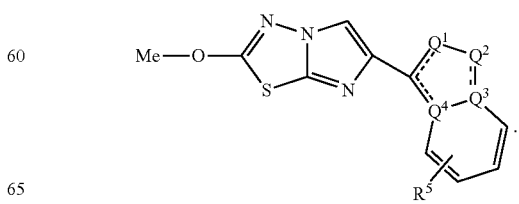

Another embodiment of the present invention is a compound of the present invention is a compound wherein $R^1$ and/or $R^2$ is aryl optionally substituted with at least one independent $R^5$.

Another embodiment is a compound of any of the above claims, wherein $R^3$ is independently methyl, alkyl, $CO_2Me$, phenyl, or substituted phenyl. Examples of substituted phenyl is where phenyl is substituted by, independently, at least one hydrogen, methyl, alkyl, $OCH_3$, $OCF_3$, $CF_3$, halogen, CN, or amide.

Another embodiment of the present invention is a compound of the following formula:

wherein:
 $Q^1$ is $CR^3$, S, O, or $NR^3$;
 $Q^3$ is $CR^2$;
 $Q^4$ is $CR^1$; and
 $R^6$ is hydrogen, methyl, alkyl, $OCH_3$, $OCF_3$, $CF_3$, halogen, CN, or amide.

Another embodiment of the present invention is a compound of the following formula:

wherein:
 $Q^1$ is $CR^3$, S, O, or $NR^3$;
 $Q^2$ is $CR^3$;
 $Q^4$ is $CR^1$; and
 $R^6$ is hydrogen, methyl, alkyl, $OCH_3$, $OCF_3$, $CF_3$, halogen, CN, or amide.

Another embodiment of the present invention is a compound of the following formula:

wherein:
 $Q^3$ is $CR^2$; and
 $Q^4$ is $CR^1$.

Another embodiment of the present invention is a compound of the following formula:

wherein:
 $Q^1$ is $CR^3$, or N; and
 $Q^2$ is $CR^3$, N—Z, S, or O.

Another embodiment of the present invention is a compound of the following formula:

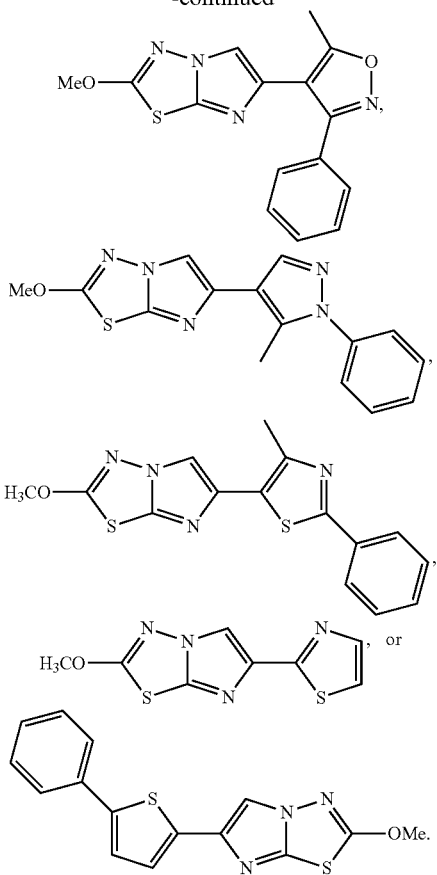

The compounds disclosed herein can include all salt forms, for example, salts of both basic groups, inter alia, amines, as well as salts of acidic groups, inter alia, carboxylic acids. The following are non-limiting examples of anions that can form salts with protonated basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: ammonium, sodium, lithium, potassium, calcium, magnesium, bismuth, lysine, and the like.

The analogs (compounds) of the present disclosure are arranged into several categories to assist the formulator in applying a rational synthetic strategy for the preparation of analogs which are not expressly exampled herein. The arrangement into categories does not imply increased or decreased efficacy for any of the compositions of matter described herein.

Some of the compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art. Alternatively, any enantiomer of a compound may be obtained by stereoselective synthesis using optically pure starting materials or reagents of known configuration by methods well known in the art.

C. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds. The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

Further disclosed herein are pharmaceutical compositions comprising one or more of the disclosed PAR4 antagonists and a pharmaceutically acceptable carrier.

Accordingly, the pharmaceutical compositions of the present invention include those that contain one or more other active ingredients, in addition to a compound of the present invention.

The above combinations include combinations of a disclosed compound not only with one other active compound, but also with two or more other active compounds. Likewise, disclosed compounds may be used in combination with other drugs that are used in the prevention, treatment, control, amelioration, or reduction of risk of the diseases or conditions for which disclosed compounds are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient can be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent may be coadministered, either in concomitant therapy or in a fixed combination.

In one aspect, the compound can be employed in combination with at least one additional therapeutic agent. In one aspect of the invention the at least one additional therapeutic agent may be an anti-platelet agent. In one aspect, the anti-platelet agent(s) are P2Y12 antagonists and/or aspirin. The P2Y12 antagonists may be clopidogrel, ticagrelor, or prasugrel. In another aspect of the invention, the at least one additional therapeutic agent(s) may be an anticoagulant. The anticoagulant agent(s) may be FXa inhibitors or thrombin inhibitors. For example, the FXa inhibitors are apixaban or rivaroxaban. Additionally, the thrombin inhibitor may be dabigatran.

In one aspect, the invention relates to pharmaceutical compositions comprising a compound having a structure represented by a formula (I):

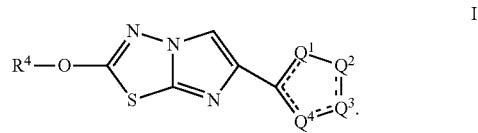

wherein:
$Q^1$ is selected from $CR^3$, N, N—Z, S, or O;
$Q^2$ is selected from $CR^3$, N, N—Z, S, or O;
$Q^3$ is selected from $CR^2$, N, N—Z, S, or O;
$Q^4$ is selected from $CR^1$, N, N—Z, S, or O;
$R^1$, $R^2$, and $R^3$ are independently selected from hydrogen, aryl, alkyl-aryl, substituted aryl, alkyl-substituted aryl, halo-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl, alkoxy, alkylalkoxy, methoxy, CN, halogen, $CONR^6R^7$, O—$CF_3$, $C(O_2)$-alkyl;
$R^1$ and $R^2$ may optionally jointly form a fused six-membered aryl or heteroaryl ring, optionally substituted with at least one $R^5$;
$R^4$ is methyl, $C_1$-$C_6$ alkyl;
$R^5$ is independently hydrogen, halogen, $C_1$-$C_6$ alkyl, cycloalkyl, alkoxy, methoxy, trifluoromethoxy, CN, amide, methyl, or trifluoromethyl;
$R^6$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;
$R^7$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl and $R^6$ and $R^7$ may join to form a 4- to 6-membered ring;
Z is optionally present and is selected from hydrogen, aryl, substituted aryl, $C_1$-$C_4$ alkyl, $C_1$-$C_3$ polyhaloalky, CN, halogen, amide, $C_1$-$C_2$ alkyl-aryl, $C_1$-$C_2$ alkyl-substituted aryl, $C_1$-$C_2$ alkyl-CN, $C_1$-$C_2$ alkyl-halogen, $C_1$-$C_2$ alkyl-amide; or a pharmaceutically acceptable salt, solvate, or polymorph thereof, and a pharmaceutically acceptable carrier.

D. Uses

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I or stereoisomers, tautomers, pharmaceutically acceptable salts, prodrug esters, or solvates thereof.

The thromboembolic disorder may be selected from the group consisting of acute coronary syndrome, unstable angina, stable angina, ST-elevated myocardial infarction, non-ST-elevated myocardial infarction, atrial fibrillation, myocardial infarction, transient ischemic attack, stroke, atherosclerosis, peripheral arterial disease, venous thrombosis, deep vein thrombosis, thrombophlebitis, arterial embolism, coronary arterial thrombosis, cerebrovascular injury, cerebral arterial thrombosis, cerebral embolism, kidney embolism, pulmonary embolism, cancer-related thrombosis, and thrombosis resulting from medical implants, devices, and procedures in which blood is exposed to an artificial surface that promotes thrombosis.

In some embodiments, the present invention includes a method of inhibiting or preventing platelet aggregation, which includes the step of administering to a subject (such as a human) in need thereof a therapeutically effective amount of a PAR4 antagonist, which is a compound of Formula I.

In some embodiments, the invention provides a method of treatment or prophylaxis of a thromboembolic disorder involving administering to a subject in need thereof (e.g., a human) a therapeutically effective amount of a compound that binds to PAR4 (such as a compound of Formula I of the invention) and inhibits PAR4 cleavage and/or signaling, wherein said subject has a dual PAR1/PAR4 platelet receptor repertoire.

In some embodiments, the present invention provides a compound of the present invention or stereoisomers, tautomers, pharmaceutically acceptable salts, solvates, or prodrug esters thereof, for use in therapy for the treatment or prophylaxis of a thromboembolic disorder.

In some embodiments, the present invention also provides the use of a compound of the present invention or stereoisomers, tautomers, pharmaceutically acceptable salts, solvates, or prodrug esters thereof, for the manufacture of a medicament for the treatment or prophylaxis of a thromboembolic disorder.

In some embodiments, compounds of the present invention may be co-administered with at least one additional drug or therapeutic agent. In certain embodiments of the preset invention, the at least one additional therapeutic agent(s) are an anti-platelet agent or a combination thereof. Examples of the anti-platelet agents include P2Y12 antagonists and/or aspirin. Preferably, the P2Y12 antagonists are clopidogrel, ticagrelor, or prasugrel. In another embodiment, the at least one additional therapeutic agent is an anticoagulant. Examples of the anticoagulant agent include FXa inhibitors or thrombin inhibitors. The FXa inhibitors may be, for example, apixaban or rivaroxaban. The thrombin inhibitor may be, for example, dabigatran.

Further examples include therapeutics such as a thrombolytic, anticoagulant or antiplatelet agent. Typically, the antithrombotic is aspirin, heparin, heparin sulfate, danaparoid sodium, clopidogrel, prasugrel, ticagrelor, cangrelor, elinogrel, cilostazol, abciximab, eptifibatide, tirofiban, dipyridamole, epoprostenol, abciximab, eptifibatide, tirofiban, beraprost, prostacyclin, iloprost, and treprostinil, aloxiprin, carbasalate calcium, indobufen, triflusal dipyridamole, picotamide, terutroban, triflusal cloricromen, ditazole, acenocoumarol, coumatetralyl, dicoumarol, ethyl biscoumacetate, phenprocoumon, warfarin, clorindione, diphenadione, phenindione, tioclomarol, defibrotide, ramatroban, antithrombin III, and/or protein C (drotrecogin alfa) or combinations thereof.

Additionally, as described above, in some embodiments compounds of the present invention are useful for treating or preventing influenza virus type A infections.

In other embodiments, compounds of the present invention may be useful in treating or preventing inflammation.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.]

E. Examples/Experimental

Some of the compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art. Alternatively, any enantiomer of a compound may be obtained by stereoselective synthesis using optically pure starting materials or reagents of known configuration by methods well known in the art.

1. Preparation of the Compounds

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

Example compounds of type 1.4 can be prepared according to Scheme 1 starting from an appropriate 5-membered or fused 5-membered ring system of type 1.1, such as thiophene, pyrrole, benzothiophene, indole, indazole, etc., acetylation with tin tetrachloride in the presence of acetic anhydride furnishes ketone 1.2. Chlorination, followed by a one-pot two step bromination and cyclization using 5-bromo-1,3,4-thiadiazol-2-amine furnishes bromide 1.3. Final displacement using methoxide base provides examples compounds of type 1.4 bearing a methyl ether.

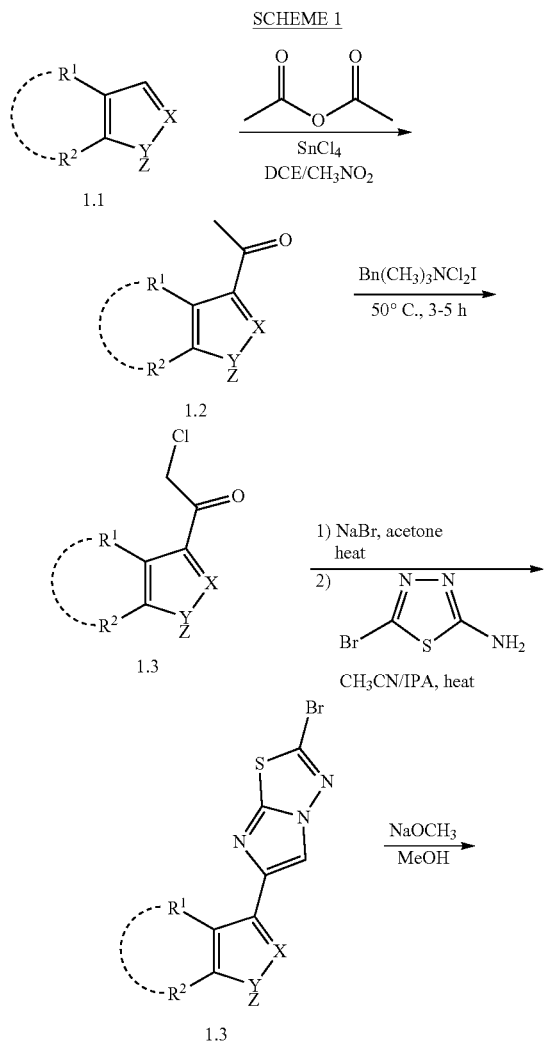

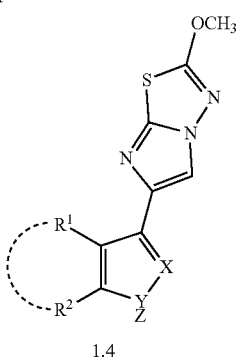

A more specific example is set forth below in Scheme 2 in the preparation of Example B1 (2.5).

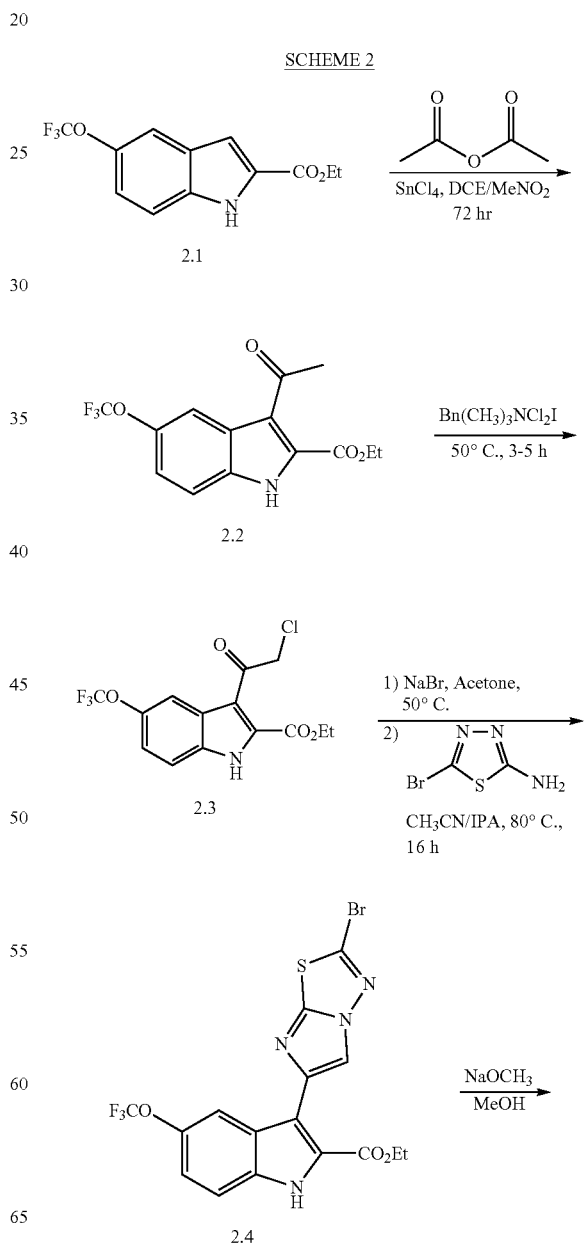

-continued

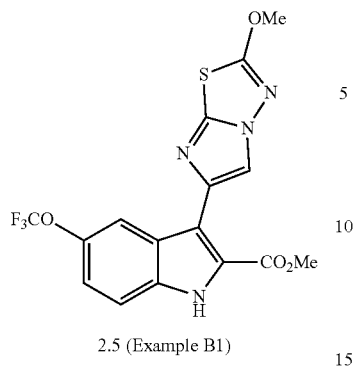

2.5 (Example B1)

Alternatively, example compounds may be obtained from commercial or readily available bromo ketones of the type 3.1 shown below in Scheme 3. The preparation of alpha-bromo ketones is well known to those skilled in the art.

SCHEME 3

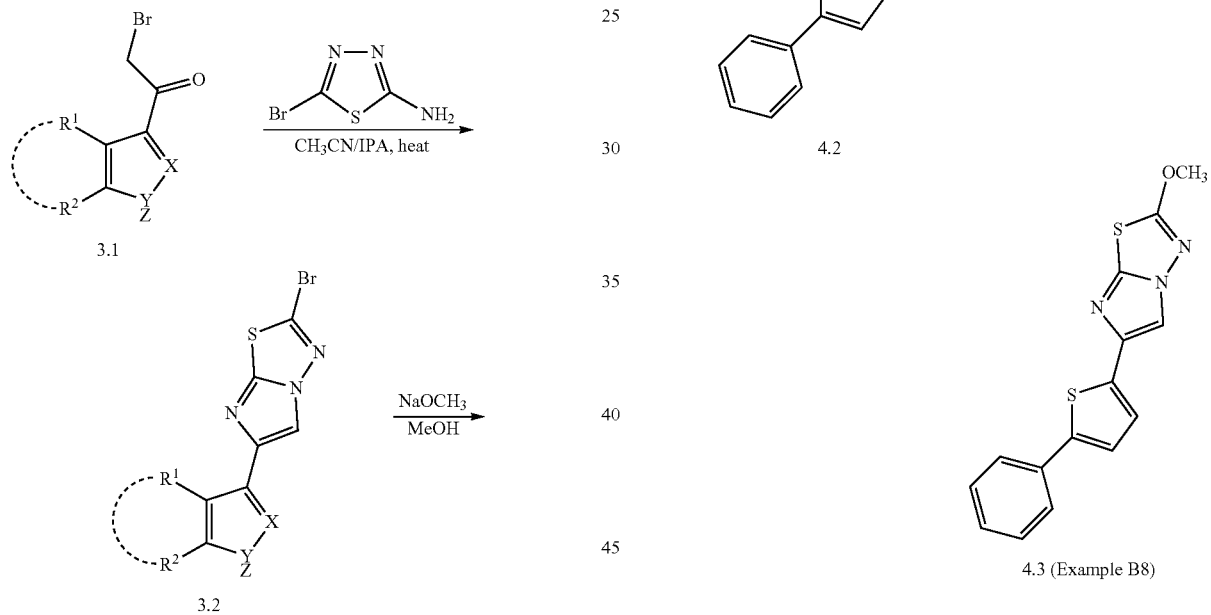

A more specific example is set forth below in Scheme 4 in the preparation of Example B3 (4.3).

SCHEME 4

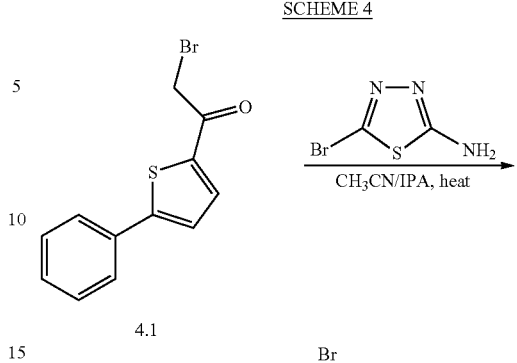

2. Experimental

Hereinafter, the term "EtOAc" means ethyl acetate, "DCM" means dichloromethane, "DIPEA" means N,N-diisopropylethylamine, "DMF" means N,N-dimethylformamide, "THF" means tetrahydrofuran, "DTBAD" means di-tert-butyl azodicarboxylate, "HATU" means 2-(7-aza-1H-benzotriazole-1-yl)-1,1,3,3-tetramethyluronium hexafluorophosphate, "LCMS" means liquid chromatography/mass spectrometry, "MeOH" means methanol, "[M+H]$^+$" means the protonated mass of the free base of the compound, "M. p." means melting point, "NMR" means nuclear magnetic resonance, "$R_t$" means retention time (in minutes), "THF" means tetrahydrofuran, "rt" means room temperature.

Microwave assisted reactions were performed in a single-mode reactor: Emrys™ Optimizer microwave reactor (Personal Chemistry A.B., currently Biotage). Hydrogenation reactions were performed in a Parr hydrogenation shaker apparatus or using a balloon at atmospheric pressure.

Analytical thin layer chromatography was performed on Analtech silica gel GF 250 micron plates using reagent grade solvents. Normal phase flash silica gel-based column chromatography was performed using ready-to-connect cartridges from ISCO, on irregular silica gel, particle size 15-40 µm on a Combi-flash Companion chromatography system from ISCO.

Low resolution mass spectra were obtained on an Agilent 1200 series 6130 mass spectrometer. High resolution mass spectra were recorded on a Waters Q-TOF API-US. Analytical HPLC was performed on an HP1100 with UV detection at 214 and 254 nm along with ELSD detection, LC/MS (J-Sphere80-C18, 3.0×50 mm, 4.1 min gradient, 5% [0.05% TFA/CH$_3$CN]:95% [0.05% TFA/H$_2$O] to 100% [0.05% TFA/CH$_3$CN]. Preparative RP-HPLC purification was performed on a custom HP1100 automated purification system with collection triggered by mass detection or using a Gilson Inc. preparative UV-based system using a Phenomenex Luna C18 column (50×30 mm I.D., 5 µm) with an acetonitrile (unmodified)-water (0.1% TFA) custom gradient.

For LC-MS-characterization of the compounds of the present invention, the following methods were used.

Method 1:

The HPLC measurement was performed using an Agilent 1200 system comprising a binary pump with degasser, an autosampler, a column oven, a diode-array detector (DAD) and a column as specified in the respective methods below. Flow from the column was split to a SQ mass spectrometer and Polymer Labs ELSD. The MS detector was configured with an ES ionization source. Nitrogen was used as the nebulizer gas. The source temperature was maintained at 350° C. Data acquisition was performed with Agilent Chemstation software. Reversed phase HPLC was carried out on a Kinetex C18 column (2.6 µm, 2.1×30 µm) from Phenomenex, with a flow rate of 1.5 mL/min, at 45° C. The gradient conditions used are: 93% A (water+0.1% TFA), 7% B (acetonitrile), to 95% B in 1.1 minutes, returning to initial conditions at 1.11 minutes. Injection volume 1 µL. Low-resolution mass spectra (single quadruple MSD detector) were acquired in electrospray mode by scanning from 100 to 700 in 0.25 seconds, step size of 0.1 and peak width of 0.03 minutes. The capillary needle voltage was 3.0 kV and the fragmentor voltage was 100V.

Method 2:

Using method 1 instrument and column conditions. The gradient conditions used are: 93% A (water+0.1% TFA), 7% B (acetonitrile), to 95% B in 2.0 minutes, returning to initial conditions at 2.11 minutes. Injection volume 1 µL. Low-resolution mass spectra (single quadruple MSD detector) were acquired in electrospray mode by scanning from 100 to 700 in 0.25 seconds, step size of 0.1 and peak width of 0.03 minutes. The capillary needle voltage was 3.0 kV and the fragmentor voltage was 100V.

Chiral purification of racemic mixtures was readily accomplished using a supercritical fluid chromatography (SFC) instrument from Thar Scientific Instruments. Chiral analytical and semi-prep SFC purification columns were from Chiral Technologies.

$^1$H and $^{13}$C NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard.

(a) Preparation of the Intermediates

Intermediate A1. Ethyl 3-(2-chloroacetyl)-5-(trifluoromethoxy)-1H-indole-2-carboxylate

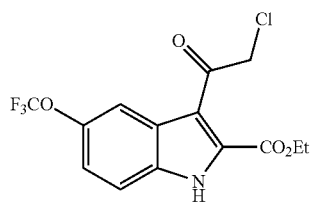 [SMILES: CCOC(=O)c1[nH]c2ccc(OC(F)(F)F)cc2c1C(=O)CCl]

Step 1. Preparation of ethyl 3-acetyl-5-(trifluoromethoxy)-1H-indole-2-carboxylate To an oven dried round bottom flask cooled under an Argon atmosphere was added a magnetic stirring bar and a solution of ethyl 5-(trifluoromethoxy)-1H-indole-2-carboxylate (0.55 mmol) in 1,2-dichloroethane (2.2 mL). The solution was cooled to 0° C. where SnCl$_4$ (0.66 mmol) was added in a single portion via syringe. After the ice bath was removed, the mixture was stirred at ambient temperature for 30 minutes after which acetic anhydride (0.55 mmol) was added in small portions to the suspension followed by nitromethane (1.6 mL). The mixture was stirred for 48 hr at room temperature and then the reaction mixture was quenched with ice cooled water. The mixture was filtered to remove inorganic precipitates and the organic material was extracted with ethyl acetate (2×5 mL). The organic phase was dried over magnesium sulfate, concentrated, and purified via silica chromatography (hexanes-20% EtOAc/Hexanes) to afford title compound in 92% yield: LC-MS [M+H]=316, RT 1.004; $^1$H NMR (400 MHz, d-CDCl$_3$) δ 9.32 (s, 1H), 8.01 (s, 1H), 7.41-7.43 (d, J=8.92 Hz, 1H), 7.23-7.26 (m, 1H), 4.47-4.52 (q, J=7.15 Hz, 3H), 2.75 (s, 3H), 1.44-1.47 (t, J=7.14, 4H).

Step 2. Preparation of ethyl 3-(2-chloroacetyl)-5-(trifluoromethoxy)-1H-indole-2-carboxylate (3)

Benzyltrimethylammonium dichloroiodate (0.81 mmol) was added to a solution of ethyl 3-acetyl-5-(trifluoromethoxy)-1H-indole-2-carboxylate from step 1 (0.54 mmol) in THF (1.8 mL) and the mixture was stirred at 50° C. for 3-5 hrs. Mixture was cooled to 0° C. and quenched with a 10% NaHCO$_3$ solution. The mixture was extracted with EtOAc (2×5 mL), washed with 5% Na$_2$S$_2$O$_{3(aq)}$, brine, and the organic layer was dried with MgSO$_4$, filtered and evaporated at reduced pressure. Purification by silica chromatography (5% EtOAc/Hexanes-30% EtOAc/Hexanes) afforded the title compound in 83% yield: LC-MS [M+H]=350, RT=1.217; $^1$H NMR (400 MHz, d-CDCl$_3$) δ 9.31 (s, 1H), 8.06 (s, 1H), 7.44-7.46 (m, 1H), 7.27-7.7.30 (m, 1H), 4.91 (s, 2H), 4.49-4.54 (q, J=7.16 Hz, 3H), 1.46-1.50 (t, J=7.16, 4H).

(b) Preparation of Representative Compounds

Example 1: (Table 1, B1) Methyl 3-(2-methoxyimidazo[2,1-b][1,3,4]thiadiazol-6-yl)-5-(trifluoromethoxy)-1H-indole-2-carboxylate

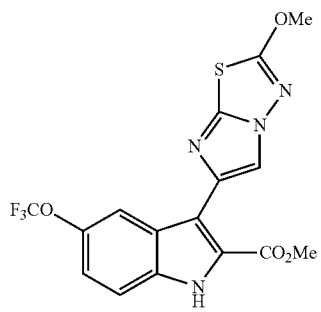 [SMILES: COC(=O)c1[nH]c2ccc(OC(F)(F)F)cc2c1-c1cn2nc(OC)sc2n1]

Step 1. Ethyl 3-(2-chloroacetyl)-5-(trifluoromethoxy)-1H-indole-2-carboxylate (Intermediate A1) was dissolved in acetone (5.4 mmol) and NaBr (1.08 mmol) was added to the solution and the reaction mixture was stirred at 50° C. for 16 hr. Upon completion, the reaction was filtered, concentrated under reduced pressure and used directly in the next reaction. A mixture of ethyl 3-(2-bromoacetyl)-5-(trifluoromethoxy)-1H-indole-2-carboxylate (0.45 mmol) and 5-bromo-1,3,4-thiadiazol-2-amine (0.68 mmol) were dissolved in CH$_3$CN/IPA (1:1; 5.6 mL) in a microwave vial that was sealed and heated to 80° C. for 18 hr. Next, the vial was placed in a Microwave for 30 minutes at 150° C. The reaction was diluted with DCM, washed with saturated NaHCO$_3$ (10 mL), brine, and dried over magnesium sulfate. Purification by silica chromatography (Hexanes-30% EtOAc/Hexanes-80% EtOAc/Hexanes) afforded the title compound in 62% yield: LC-MS [M+H]=476, RT=1.338; $^1$H NMR (400 MHz, d-CDCl$_3$) δ 9.21 (s, 1H), 8.62 (s, 1H), 8.43-8.44 (m, 1H), 7.37-7.40 (d, J=8.92 Hz, 1H), 7.22-7.25 (m, 1H), 4.41-4.46 (q, J=7.14 Hz, 3H), 1.41-1.44 (t, J=7.14, 4H).

Step 2. A solution of ethyl 3-(2-bromoimidazo[2,1-b][1,3,4]thiadiazol-6-yl)-5-(trifluoromethoxy)-1H-indole-2-carboxylate (0.28 mmol) in a mixture of DCM/MeOH (4:1; 12.5 mL) was treated at 22° C. with a 25 wt. % solution of NaOMe (1.1 mmol) in MeOH. Next, an additional 2.5 mL of MeOH was added and the reaction was stirred for 1 hr. Upon completion, the reaction mixture was quenched by addition of 1% HCl (5 mL) followed by addition of sat. NaHCO$_3$ (5 mL). Solvent was evaporated and the residue was diluted with DCM, washed with brine, dried with magnesium sulfate and evaporated. Normal phase chromatography on silica gel (100% DCM-5% EtOAc/DCM-30% EtOAc/DCM) afforded title compound in 38% yield as methyl ester: LC-MS [M+H]=413, RT=1.131; $^1$H NMR (400 MHz, chloroform-d) δ 9.08 (s, 1H), 8.44 (s, 1H), 8.39 (s, 1H), 7.36-7.39 (d, J=8.88 Hz, 1H), 7.22-7.24 (d, J=8.76 Hz, 1H), 4.2165 (s, 1H), 3.96 (s, 1H).

Example 2: (B8, Table 1) 2-Methoxy-6-(5-phenylthiophen-2-yl)imidazo[2,1-b][1,3,4]thiadiazole

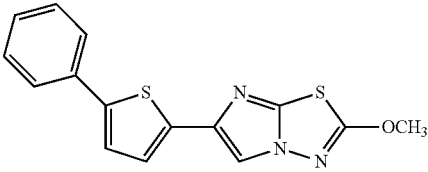 [SMILES: COc1nn2cc(-c3ccc(-c4ccccc4)s3)nc2s1]

Step 1. A mixture of commercially available 2-bromo-1-(5-phenylthiophen-2-yl)ethan-1-one (0.10 mmol) and 5-bromo-1,3,4-thiadiazol-2-amine (0.15 mmol) were dissolved in CH$_3$CN/IPA (1:1; 1.3 mL) in a microwave vial that was sealed and heated to 80° C. for 18 hr. Next, the vial was placed in a Microwave for 30 minutes at 150° C. The reaction was diluted with DCM, washed with saturated NaHCO$_3$ (10 mL), brine, and the organic layer was passed through a phase separator. The organic layer was concentrated under reduced pressure and the crude product was used directly in the next step without purification.

Step 2. A solution of 2-bromo-6-(5-phenylthiophen-2-yl)imidazo[2,1-b][1,3,4]thiadiazole (0.10 mmol) in a mixture of DCM/MeOH (4:1; 5 mL) was treated at 22° C. with a 25 wt. % solution of NaOMe (0.40 mmol) in MeOH. Next, an additional 1 mL of MeOH was added and the reaction was stirred for 1 hr. Upon completion as determined by LCMS, the reaction mixture was quenched by addition of 1% HCl (5 mL) followed by addition of saturated NaHCO$_3$ (5 mL). The aqueous layer was extracted with DCM (3×3 mL) and the organic layers were pooled then passed through a phase separator. Solvent was evaporated and the residue was re-suspended in 1 mL of DMSO. Compound was purified on a Gilson preparative reversed-phase HPLC system comprised of a 333 aqueous pump with solvent-selection valve, 334 organic pump, GX-271 or GX-281 liquid hander, two column switching valves, and a 155 UV detector. Fraction collection was triggered by absorbance at 215 nm, with absorbance at 254 nm monitored. Column: Phenomenex Axia-packed Gemini C18, 30×50 mm, 5 μm. Gradient conditions: Hold at 70% CH$_3$CN in H$_2$O (0.05% v/v NH$_4$OH) for 0.75 min, 70% to 100% CH$_3$CN in H$_2$O (0.05% v/v NH$_4$OH) over 4 min, hold at 95% CH$_3$CN in H$_2$O (0.05% v/v NH$_4$OH) for 1 min, 50 mL/min, 23° C.: LC-MS [M+H]=314, RT=1.298; $^1$H NMR (400 MHz, Acetonitrile-d$_3$) δ 7.66 (s, 1H), 7.35-7.36 (m, 1H), 7.33-7.34 (m, 1H), 7.07-7.11 (m, 2H), 7.03-7.04 (d, J=3.73 Hz, 1H), 6.98-7.01 (dt, J$_1$=7.30 Hz, J$_2$=1.11 HZ, 1H), 6.97-6.98 (d, J=3.73 Hz, 1H), 3.86 (s, 3H).

(c) Characterization of the Exemplary Compounds

The compounds of formula I below in Table 1 were synthesized with methods identical or analogous to those described herein. The Synthetic Example indicated in Table I refers to the compound identified above and corresponding synthetic method described therein. The requisite starting materials were commercially available, described in the literature, or readily synthesized by one skilled in the art of organic synthesis. The mass spectrometry data were obtained using either General LC-MS Method 1 or General LC-MS Method 2 as described above. LC-MS [M+H]$^+$ means the protonated mass of the free base of the compound.

TABLE 1

I.

| No. | Compound | LC-MS [M + H] | Retention time | Synthetic Example/ Scheme* |
|---|---|---|---|---|
| B1 | | 413 | 1.057 | Ex. 1(B1)/ Scheme 1-2 |
| B2 | | 333 | 1.221 | Ex. 2 (B8)/ Scheme 3 |
| B3 | | 288 | 1.198 | Ex. 2 (B8)/ Scheme 3-4 |
| B4 | | 313 | 1.081 | Ex. 2 (B8)/ Scheme 3 |
| B5 | | 312 | 1.024 | Ex. 2 (B8)/ Scheme 3 |
| B6 | | 329 | 1.103 | Ex. 2 (B8)/ Scheme 3 |

TABLE 1-continued

[Structure I with MeO-imidazo[2,1-b][1,3,4]thiadiazole connected to a 5-membered ring with X, Y, Z, R¹, R²]

I.

| No. | Compound | LC-MS [M + H] | Retention time | Synthetic Example/ Scheme* |
|---|---|---|---|---|
| B7 | [structure: H₃CO-imidazothiadiazole-thiazole] | 239 | 0.689 | Ex. 2 (B8)/ Scheme 3 |
| B8 | [structure: phenyl-thiophene-imidazothiadiazole-OMe] | 314 | 1.252 | Ex. 2/ Scheme 3-4 |

3. Assay Descriptions

PAC-1 Binding assay: 60 μL of washed platelets (Tyrodes buffer containing 0.1% BSA) at a concentration of $0.15 \times 10^8$ platelets/mL were added to 5 mL round bottom polystyrene tubes (BD, Franklin Lakes, N.J.). FITC conjugated PAC-1 (BD Biosciences, San Jose, Calif.) antibody was diluted (to the manufacturers recommended concentration) in Tyrode's buffer containing 0.1% BSA. 40 μL of diluted antibody was added to the platelets and allowed to incubate for 5 minutes. Platelets were pre-treated with indicated concentrations of antagonist or DMSO control for 5 minutes followed by addition of PAR-1-AP (GL Biochem, Shanghai, China) or PAR-4-AP for 10 minutes. Platelet activity was quenched by the addition ice cold 1.5% paraformaldehyde followed by dilution in 1× phosphate buffered saline. The final DMSO concentration was 0.5%. Platelets were stored up to 18 hours at 4° C. before flow cytometric analysis. Analysis was carried out on a BD FACS Canto II (Franklin Lakes, N.J.). Fluorescent intensity was determined for 100,000 events within the platelet gate. Data was collected and analyzed via FACS DiVa software. Flow cytometric data analysis was conducted by the following method. The DMSO-vehicle treated control was subtracted from each data point. 100% response for PAR-4-AP was determined for each individual as the DMSO treated control stimulated with either 200 μM PAR-4-AP, or 20 μM PAR-1-AP. Data was plotted in GraphPad PRISM v.5.0. For compounds with a notable reduction in PAC-1 binding response, a dose response curves and subsequent $IC_{50}$ values were generated using the inhibitory sigmoidal dose response 'variable slope' parameter. PAR-4 results were plotted as mean±SEM.

IV. In Vitro Activity of Representative PAR-4 Antagonists

TABLE 2

| Example | PAR-4 AP % Max PAC-1 binding (10 μM)/$IC_{50}$ [M] | γ-thrombin % Max PAC-1 binding (316 nM) |
|---|---|---|
| B1 | <1%/2.11E−06 | 100 |
| B2 | 34%/1.93E−06 | 94 |
| B3 | <1%/4.58E−07 | 99 |
| B4 | 56%/NT | 93 |
| B5 | 2.6%/1.53E−06 | 95 |
| B6 | <1%/6.98E−08 | 92 |
| B7 | 94%/NT | 98 |
| B8 | <1%/7.46E−09 | 78 |

We claim:

1. A compound of the following formula (I):

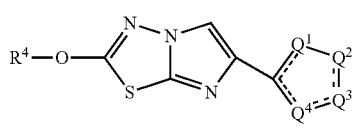

I wherein:
- $Q^1$ is selected from $CR^3$, N, N-Z, or S;
- $Q^2$ is selected from $CR^3$, N, N-Z, or S;
- $Q^3$ is selected from $CR^2$, N, N-Z, or S;
- $Q^4$ is selected from $CR^1$, N, N-Z, S, or O, provided that when $Q^4$ is O then $Q^3$ is N;
- $R^1$, $R^2$, and $R^3$ are independently selected from hydrogen, aryl, alkyl-aryl, substituted aryl, alkyl-substituted aryl, halo-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl, alkoxy, alkylalkoxy, methoxy, CN, halogen, CONR$^6$R$^7$, O-CF$_3$, and C(O$_2$)-alkyl; or R$^1$ and R$^2$ may join together to form a fused six-membered aryl or heteroaryl ring, optionally substituted with at least one R$^5$;

R$^4$ is methyl, or C$_1$-C$_6$ alkyl;

R$^5$ is independently hydrogen, halogen, C$_1$-C$_6$ alkyl, cycloalkyl, alkoxy, methoxy, trifluoromethoxy, CN, amide, methyl, or trifluoromethyl;

R$^6$ is independently selected from hydrogen, aryl, alkyl-aryl, substituted aryl, alkyl-substituted aryl, methyl, C$_1$-C$_{10}$ alkyl, C$_1$-C$_3$ polyhaloalkyl, aryloxy C$_1$-C$_2$ alkyl, cycloalkyl, alkylcycloalkyl; or R$^6$ and R$^7$ may join to form a 4- to 6-membered ring;

R$^7$ is independently selected from hydrogen, aryl, alkyl-aryl, substituted aryl, alkyl-substituted aryl, methyl, C$_1$-C$_{10}$ alkyl, C$_1$-C$_3$ polyhaloalkyl, aryloxy C$_1$-C$_2$ alkyl, cycloalkyl, alkylcycloalkyl; or R$^6$ and R$^7$ may join to form a 4- to 6-membered ring;

Z is optionally present and is selected from hydrogen, aryl, substituted aryl, C$_1$-C$_4$ alkyl, C$_1$-C$_3$ polyhaloalkyl, CN, halogen, amide, C$_1$-C$_2$ alkyl-aryl, C$_1$-C$_2$ alkyl-substituted aryl, C$_1$-C$_2$ alkyl-CN, C$_1$-C$_2$ alkyl-halogen, or C$_1$-C$_2$ alkyl-amide;

or a pharmaceutically acceptable salt, solvate, or polymorph thereof.

2. A compound of claim 1, wherein:
Q$^1$ is CR$^3$, N, or S; and
Q$^2$ is S, or N-Z.

3. A compound of claim 1, wherein:
Q$^1$ is CR$^3$;
Q$^2$ is N—Z;
Q$^3$ is CR$^2$;
Q$^4$ is CR$^1$; and
R$^1$ and R$^2$ together form a six-membered aryl.

4. A compound of claim 1, wherein:
Q$^1$ is CR$^3$;
Q$^2$ is CR$^3$;
Q$^3$ is N; and
Q$^4$ is O.

5. A compound of claim 1, wherein:
Q$^1$ is CR$^3$;
Q$^2$ is S;
Q$^3$ is CR$^2$;
Q$^4$ is CR$^1$; and
R$^1$ and R$^2$ together form a six-membered aryl.

6. A compound of claim 1, wherein:
Q$^1$ is CR$^3$;
Q$^3$ is N; and
Q$^4$ is CR$^1$.

7. A compound of claim 1, wherein:
Q$^1$ is CR$^3$;
Q$^2$ is N;
Q$^3$ is N; and
Q$^4$ is CR$^1$.

8. A compound of claim 1, wherein:
Q$^1$ is CR$^3$;
Q$^2$ is N;
Q$^3$ is CR$^2$;
Q$^4$ is S.

9. A compound of claim 1, wherein:
Q$^1$ is N;
Q$^2$ is CR$^3$;
Q$^3$ is CR$^2$;
Q$^4$ is S.

10. A compound of claim 1, wherein:
Q$^1$ is S;
Q$^2$ is CR$^3$;
Q$^3$ is CR$^2$; and
Q$^4$ is CR$^1$.

11. A compound of claim 1, wherein:
Q$^1$ is S, or N-Z;
Q$^2$ is CR$^3$;
Q$^3$ is CR$^2$; and
Q$^4$ is CR$^1$.

12. A compound of claim 1, wherein:
Q$^1$ is N;
Q$^2$ is N-Z
Q$^3$ is CR$^2$; and
Q$^4$ is CR$^1$.

13. A compound of claim 1, wherein:
Q$^1$ is CR$^3$ or N;
Q$^2$ is N—Z, or S;
Q$^3$ is CR$^2$;
Q$^4$ is CR$^1$; and
R$^1$ and R$^2$ together form a six-membered aryl.

14. A compound of claim 1, of the following formula:

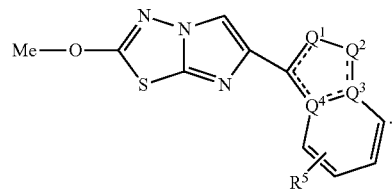

15. A compound of claim 1, wherein R$^1$ and/or R$^2$ is aryl optionally substituted with at least one independent R$^5$.

16. A compound of claim 1, wherein R$^3$ is independently methyl, C$_1$-C$_{10}$ alkyl, CO$_2$Me, phenyl, or substituted phenyl.

17. A compound of claim 16, wherein phenyl is substituted by, independently, at least one hydrogen, methyl, alkyl, OCH$_3$, OCF$_3$, CF$_3$, halogen, CN, or amide.

18. A compound of claim 1, of the following formula:

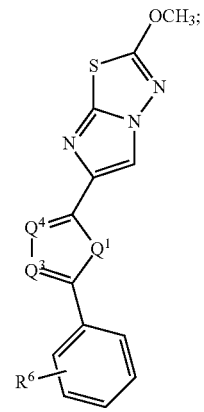

wherein:
Q$^1$ is CR$^3$, S, or N-Z;
Q$^3$ is CR$^2$;
Q$^4$ is CR$^1$; and
R$^6$ is hydrogen, methyl, alkyl, OCH$_3$, OCF$_3$, CF$_3$, halogen, CN, or amide.

19. A compound of claim 1, of the following formula:

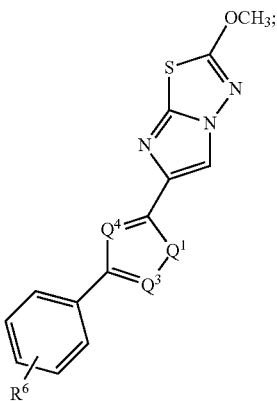

wherein:
Q$^1$ is CR$^3$, S, or N-Z;
Q$^2$ is CR$^3$;
Q$^4$ is CR$^1$; and
R$^6$ is hydrogen, methyl, alkyl, OCH$_3$, OCF$_3$, CF$_3$, halogen, CN, or amide.

20. A compound of claim 1, of the following formula:

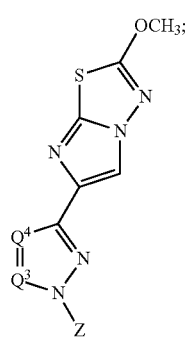

wherein:
Q$^3$ is CR$^2$; and
Q$^4$ is CR$^1$.

21. A compound of the following formula:

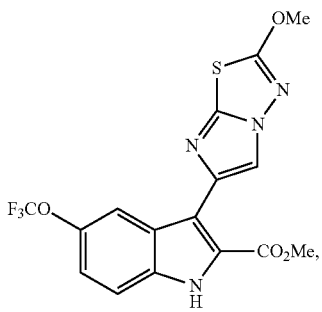

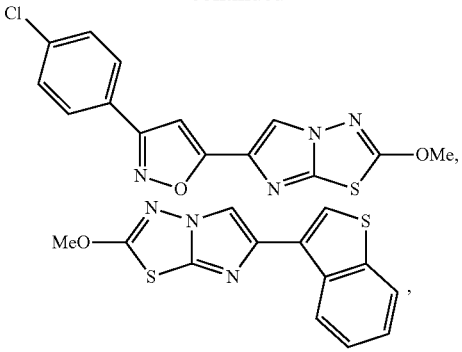

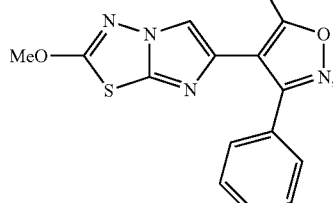

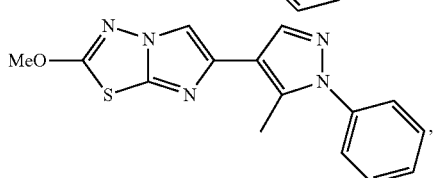

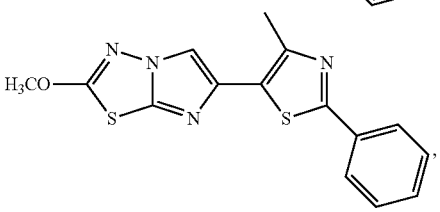

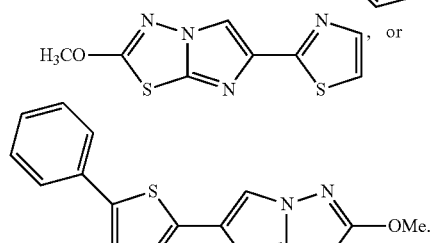

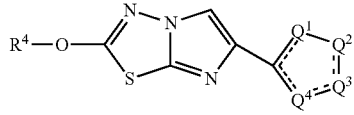

22. A composition comprising a compound of the following formula (I):

$$R^4-O\underset{S}{\overset{N-N}{\bigcirc}}\underset{N}{\overset{}{\bigcirc}}\underset{Q^4=Q^3}{\overset{Q^1-Q^2}{\bigcirc}} \quad I$$

wherein:
Q$^1$ is selected from CR$^3$, N, N-Z, or S;
Q$^2$ is selected from CR$^3$, N, N-Z, or S;
Q$^3$ is selected from CR$^2$, N, N-Z, or S;
Q$^4$ is selected from CR$^1$, N, N-Z, S, or O, provided that when Q$^4$ is O then Q$^3$ is N;
R$^1$, R$^2$, and R$^3$ are independently selected from hydrogen, aryl, alkyl-aryl, substituted aryl, alkyl-substituted aryl, halo-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl, alkoxy, alkylalkoxy, methoxy, CN, halogen, $CONR^6R^7$, O-$CF_3$, and $C(O_2)$-alkyl; or $R^1$ and $R^2$ may join together to form a fused six-membered aryl or heteroaryl ring, optionally substituted with at least one $R^5$;

$R^4$ is methyl, or $C_1$-$C_6$ alkyl;

$R^5$ is independently hydrogen, halogen, $C_1$-$C_6$ alkyl, cycloalkyl, alkoxy, methoxy, trifluoromethoxy, CN, amide, methyl, or trifluoromethyl;

$R^6$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl; or $R^6$ and $R^7$ may join to form a 4- to 6-membered ring;

$R^7$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl; or $R^6$ and $R^7$ may join to form a 4- to 6-membered ring;

Z is optionally present and is selected from hydrogen, aryl, substituted aryl, $C_1$-$C_4$ alkyl, $C_1$-$C_3$ polyhaloalkyl, CN, halogen, amide, $C_1$-$C_2$ alkyl-aryl, $C_1$-$C_2$ alkyl-substituted aryl, $C_1$-$C_2$ alkyl-CN, $C_1$-$C_2$ alkyl-halogen, or $C_1$-$C_2$ alkyl-amide;

or a pharmaceutically acceptable salt, solvate, or polymorph thereof; and a pharmaceutically acceptable carrier.

23. A method of treating thromboembolic disorder, comprising administering to a patient in need thereof an effective amount of a composition that includes a compound of the following formula (I):

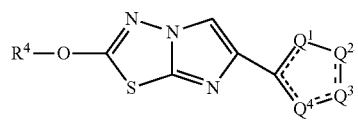

I wherein:

$Q^1$ is selected from $CR^3$, N, N-Z, or S;
$Q^2$ is selected from $CR^3$, N, N-Z, or S;
$Q^3$ is selected from $CR^2$, N, N-Z, or S;
$Q^4$ is selected from $CR^1$, N, N-Z, S, or O, provided that when $Q^4$ is O then $Q^3$ is N;

$R^1$, $R^2$, and $R^3$ are independently selected from hydrogen, aryl, alkyl-aryl, substituted aryl, alkyl-substituted aryl, halo-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl, alkoxy, alkylalkoxy, methoxy, CN, halogen, $CONR^6R^7$, O-$CF_3$, and $C(O_2)$-alkyl; or $R^1$ and $R^2$ may join together to form a fused six-membered aryl or heteroaryl ring, optionally substituted with at least one $R^5$;

$R^4$ is methyl, or $C_1$-$C_6$ alkyl;

$R^5$ is independently hydrogen, halogen, $C_1$-$C_6$ alkyl, cycloalkyl, alkoxy, methoxy, trifluoromethoxy, CN, amide, methyl, or trifluoromethyl;

$R^6$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl; or $R^6$ and $R^7$ may join to form a 4- to 6-membered ring;

$R^7$ is independently selected from hydrogen, aryl, alkyl-aryl, substituted aryl, alkyl-substituted aryl, methyl, $C_1$-$C_{10}$ alkyl, $C_1$-$C_3$ polyhaloalkyl, aryloxy $C_1$-$C_2$ alkyl, cycloalkyl, alkylcycloalkyl, or and $R^6$ and $R^7$ may join to form a 4- to 6-membered ring;

Z is optionally present and is selected from hydrogen, aryl, substituted aryl, $C_1$-$C_4$ alkyl, $C_1$-$C_3$ polyhaloalkyl, CN, halogen, amide, $C_1$-$C_2$ alkyl-aryl, $C_1$-$C_2$ alkyl-substituted aryl, $C_1$-$C_2$ alkyl-CN, $C_1$-$C_2$ alkyl-halogen, or $C_1$-$C_2$ alkyl-amide;

or a pharmaceutically acceptable salt, solvate, or polymorph thereof; and a pharmaceutically acceptable carrier.

24. A method of inhibiting PAR-4 activity, comprising administering to a patient in need thereof an effective amount of a composition that includes a compound of claim 1, and a pharmaceutically acceptable carrier.

25. A method of treating influenza, comprising administering to a patient in need thereof an effective amount of a composition that includes a compound of claim 1, and a pharmaceutically acceptable carrier.

* * * * *

UNITED STATES PATENT AND TRADEMARK OFFICE
CERTIFICATE OF CORRECTION

PATENT NO. : 9,963,466 B2
APPLICATION NO. : 15/452686
DATED : May 8, 2018
INVENTOR(S) : Hamm et al.

It is certified that error appears in the above-identified patent and that said Letters Patent is hereby corrected as shown below:

In the Specification

At Column 1, Lines 12-17 replace the second paragraph with the following:
Government Support
This invention was made with government support under grant numbers NS081669 and NS082198 awarded by the National Institutes of Health. The government has certain rights in the invention.

Signed and Sealed this
Tenth Day of December, 2019

Andrei Iancu
*Director of the United States Patent and Trademark Office*